United States Patent
Wang et al.

(10) Patent No.: US 9,938,235 B2
(45) Date of Patent: Apr. 10, 2018

(54) COMPOUNDS WITH NEURAL PROTECTIVE EFFECT, AND PREPARATION AND USE THEREOF

(71) Applicant: GUANGZHOU MAGPIE PHARMACEUTICAL CO., LTD., Guangzhou (CN)

(72) Inventors: Yuqiang Wang, Guangzhou (CN); Moussa B. H. Youdim, Guangzhou (CN); Yewei Sun, Guangzhou (CN); Zaizun Zhang, Guangzhou (CN); Gaoxiao Zhang, Guangzhou (CN); Pei Yu, Guangzhou (CN); Peng Yi, Guangzhou (CN); Ming Lang, Guangzhou (CN); Wei Liu, Guangzhou (CN)

( * ) Notice: Subject to any disclaimer, the term of this patent is extended or adjusted under 35 U.S.C. 154(b) by 0 days.

(21) Appl. No.: 14/999,766

(22) PCT Filed: Mar. 2, 2015

(86) PCT No.: PCT/CN2015/000193
§ 371 (c)(1),
(2) Date: Jun. 24, 2016

(87) PCT Pub. No.: WO2015/109935
PCT Pub. Date: Jul. 30, 2015

(65) Prior Publication Data
US 2016/0326099 A1 Nov. 10, 2016

(30) Foreign Application Priority Data
Jan. 23, 2014 (CN) .......................... 2014 1 0033815

(51) Int. Cl.
*C07C 271/44* (2006.01)
*C07C 291/02* (2006.01)
*C07D 241/12* (2006.01)

(52) U.S. Cl.
CPC .......... *C07C 271/44* (2013.01); *C07C 291/02* (2013.01); *C07D 241/12* (2013.01); *C07C 2602/08* (2017.05)

(58) Field of Classification Search
CPC .................................................. C07C 271/44
See application file for complete search history.

*Primary Examiner* — Brian McDowell
(74) *Attorney, Agent, or Firm* — Charles Liu

(57) ABSTRACT

The invention generally relates to compounds of formula (I) with neural protective effect, and preparation and uses thereof.

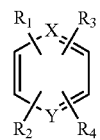

(I)

The compounds have multiple mechanisms or functions, for example, inhibition of monoamine oxidase and cholinesterase, scavenging of free radicals, and protection of cells such as nerve cells. The compounds can be used for manufacture of medicaments of cell protection, for prevention and/or treatment of monoamine oxidase, cholinesterase and free radicals related diseases, for example, neurodegenerative diseases such as Alzheimer's disease, Parkinson's disease and stroke, and free-radical related diseases such as heart disease, myocardial ischemia, diabetes and other cardiovascular and cerebrovascular diseases.

6 Claims, 15 Drawing Sheets

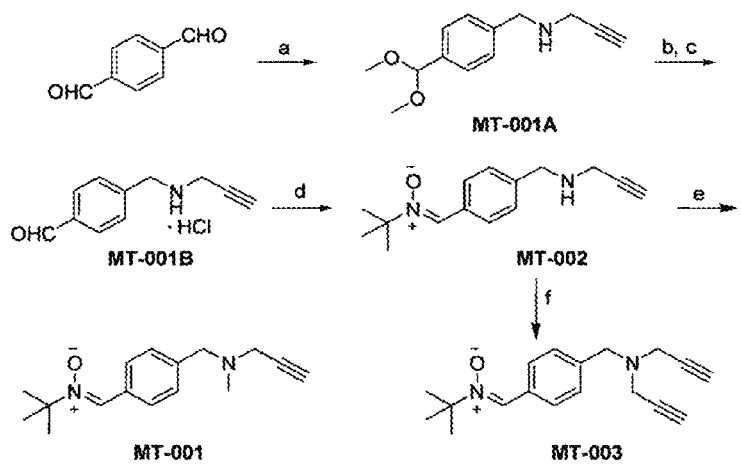

Reagents and conditions: (a) Propargylamine, NaBH$_3$CN, HCl, CH$_3$OH, reflux; (b) HCl:H$_2$O:THF=1:6:7, rt; (c) HCl/EtOAc, rt; (d) OHNHC(CH$_3$)$_3$, C$_2$H$_5$OH, rt. (e) CH$_3$I, CH$_3$CN, rt; (f) Propargyl bromide, NaHCO$_3$, CH$_3$OH, reflux.

FIG.1

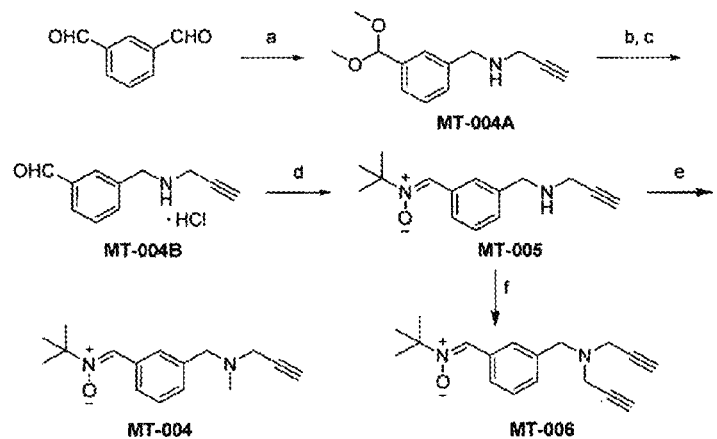

Reagents and conditions: (a) Propargylamine, NaBH$_3$CN, HCl, CH$_3$OH, reflux; (b) HCl:H$_2$O:THF=1:6:7, rt; (c) HCl/EtOAc, rt; (d) OHNHC(CH$_3$)$_3$, C$_2$H$_5$OH, rt. (e) CH$_3$I, CH$_3$CN, rt; (f) Propargyl bromide, NaHCO$_3$, CH$_3$OH, reflux.

FIG.2

Reagents and conditions: (a) OHNHC(CH₃)₃, C₂H₅OH, reflux; (b) MeEtNCOCl, CH₂Cl₂, NaOH, rt.

Reagents and conditions: (a) SeO₂, Dioxane, 107 °C; (b) STAB-H, DCE, rt; (c) STAB-H, DCE, Propargylamine, rt; (d) (Boc)₂O, NaHCO₃, THF, rt; (e) MeEtNCOCl, CH₂Cl₂, NaH, rt; (f) TFA, CH₂Cl₂, rt. (g) CH₃I, NaHCO₃, CH₃OH, rt; (h) Propargyl bromide, NaHCO₃, CH₃OH, rt.

Reagents and conditions: (a) H₂O₂, AcOH, 70 °C, 8 h; (b) Ac₂O, 125 °C, 3 h; (c) NaOH, rt, 5h; (d) MnO₂, EtOH, reflux, 3h; (e) STAB-H, DCE, Propargylamine, rt, 4 h; (f) CH₃I, K₂CO₃, acetone, reflux, 3 h; (g) Propargyl bromide, K₂CO₃, CH₃OH, rt, 3 h.

Reagents and conditions: (a) ethylene glycol, PTSA, toluene, reflux, 2.5h; (b) STAB-H, DCE, Propargylamine, rt, 4 h; (c) CH₃I, K₂CO₃, acetone, reflux, 3 h; (d) HCl/H₂O/THF (1:6:7), rt, 5 h. (e) OHNHC(CH₃)₃, C₂H₅OH, rt, 5 h.

Reagents and conditions: (a) Propargyl bromide, $K_2CO_3$, $CH_3OH$, rt, 3 h. (b) $HCl/H_2O/$ THF (1:6:7), rt. 5 h. (c) $OHNHC(CH_3)_3$, $C_2H_5OH$, rt, 5 h.

Reagents and conditions: (a) MeEtNCOCl, $CH_2Cl_2$, NaH, rt, 5h;

Reagents and conditions: (a) $OHNHC(CH_3)_3$, $C_2H_5OH$, rt, 7 h. (b) MeEtNCOCl, $CH_2Cl_2$, NaH, rt, 5h;

Reagents and conditions: (a) Propargylamine, NaBH$_3$CN, CH$_3$OH, reflux, 8h, 85 %. (b) (Boc)$_2$O, Et$_3$N, THF, r.t., 48h, 71 %. (c) (HCHO)n, MgCl$_2$, CH$_3$CN, reflux, 2h, 99 %; (d) TFA, CH$_2$Cl$_2$, r.t., 4h, 95%; (e) Tert-butylhydroxylamine, EtOH, r.t., 20h, 89 %; (f) N-Ethyl-N-methylcarbamoyl Chloride, NaOH, CH$_2$Cl$_2$, r.t., 3h, 88 %. (g) CH$_3$I, NaHCO$_3$, Acetone, r.t., 2h, 72 %; (h) Propargyl bromide, NaOH, CH$_3$OH, r.t., 8h, 99 %;

Reagents and conditions: (a) Propargyl bromide, NaHCO$_3$, CH$_3$OH, reflux, 10h, 68 %; (b) (HCHO)n, MgCl$_2$, CH$_3$CN, reflux, 2h, 98%; (c) Tert-butylhydroxylamine, EtOH, r.t., 10h, 90 %; (d) N-Ethyl-N-methylcarbamoyl Chloride, NaOH, CH$_2$Cl$_2$, r.t., 3h, 98 %.

Reagents and conditions: (a) TFAA, CH$_2$Cl$_2$, 0 °C, 67 %; (b) Ethyl oxalyl monochloride, AlCl$_3$, ClCH$_2$CH$_2$Cl, r.t., 9h, 90 %; (c) NaBH$_4$, EtOH, r.t., 3h, 96 %; (d) H$_5$IO$_6$, 50% EtOH, r.t., 10 min, 100 %; (e) Propargyl bromide, NaOH, DMF, r.t., 8h, 85 %; (f) 0.2 N NaOH, 50 % EtOH, r.t., 3h, 91 %; (g) Tert-butylhydroxylamine, EtOH, r.t., 20h, 90 %; (h) CH$_3$I, NaHCO$_3$, Acetone, r.t., 2h, 61 %; (i) Tert-butylhydroxylamine, EtOH, r.t., 18h, 97 %; (j) 0.2 N NaOH, 50% EtOH, r.t., 3h, 78 %.

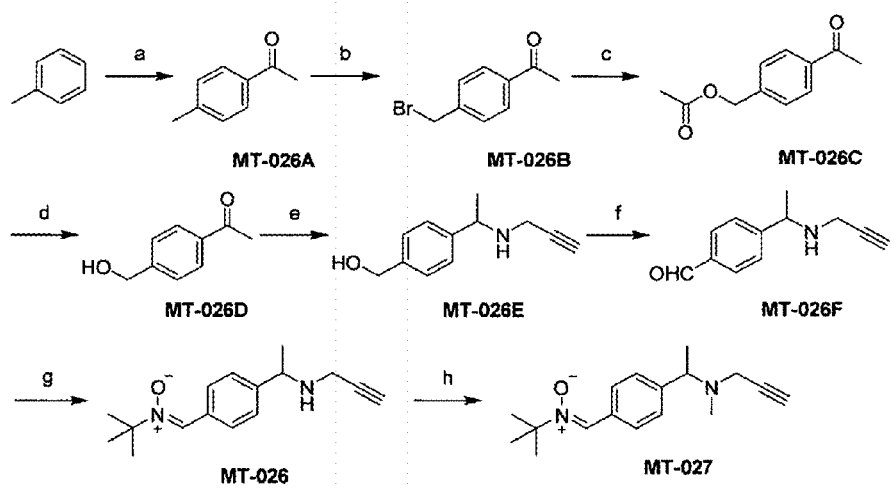

Reagents and conditions: (a) Acetyl chloride, AlCl$_3$, r.t., 90 %; (b) NBS, BPO, CCl$_4$, hv, reflux, 3h, 91 %; (c) Sodium acetate anhydrous, acetic acid, reflux, 8h, 100 %; (d) NaOH, 70 % CH$_3$OH, r.t., 30 min, 97%; (e) Propargylamine, NaBH$_3$CN, CH$_3$OH, reflux, 8h, 77 %. (f) MnO$_2$, acetic ether, reflux, 5h, 94 %; (g) Tert- butylhydroxylamine, EtOH, r.t., 20h, 90 %; (h) CH$_3$I, NaHCO$_3$, Acetone, r.t., 2h, 70 %;

FIG.13

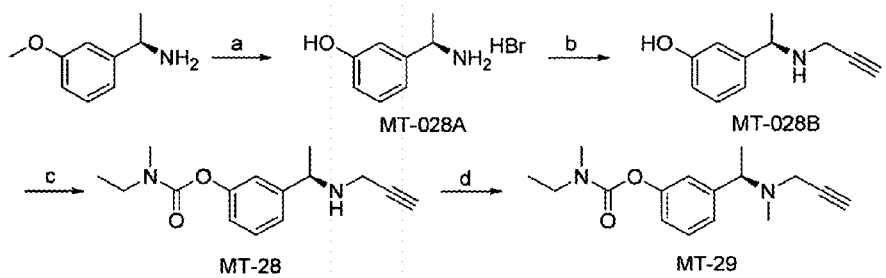

Reagents and conditions: (a) HBr, 100 °C, 6h; (b) Propargylamine, MeCN, r.t. 36h; (c) MeEtNCOCl, CH$_2$Cl$_2$, NaH, rt, 24h; (d) CH$_3$I, NaHCO$_3$, acetone, rt. 6h.

FIG.14

Reagents and conditions: (a) HBr, 100 °C, 6h; (b) Propargylamine, MeCN, r.t. 36h; (c) MeEtNCOCl, CH$_2$Cl$_2$, NaH, rt, 24h; (d) CH$_3$I, NaHCO$_3$, acetone, rt. 6h.

Reagents and conditions: (a) MeEtNCOCl, CH$_2$Cl$_2$, NaH, rt; (b) Propargyl bromide, NaHCO$_3$, CH$_3$OH, 68 °C; (c) CH$_3$I, NaHCO$_3$, CH$_3$OH, rt.

| Compound | MAO-A/B Inhibiting Activity (IC50 µM) | |
|---|---|---|
| | MAO-A | MAO-B |
| MT-002 | > 100 | 14.73 ± 0.59 |
| MT-019 | > 100 | 20.33 ± 0.81 |
| MT-020 | > 100 | 1.05 ± 0.16 |
| HMW-1 | > 10 | > 10 |
| HMW-2 | 0.029 ± 0.002 | 0.47 ± 0.02 |
| HMW-3 | 0.74 ± 0.04 | > 10 |

FIG.19

| Organ | MAO-A/B Inhibiting Activity (% of control) | |
|---|---|---|
| | MAO-A | MAO-B |
| Cerebellum | 80.5 ± 13.4#* | 67.0 ± 9.1# |
| Liver | 21.2 ± 5.2# | 3.5 ± 6.5 |
| Intestinum tenue | 91.7 ± 6.4#* | 65.2 ± 5.2# |

FIG.20

| MAO-A/B Inhibiting Activity (% of control) | Dosage (mg/kg) | | | | | |
|---|---|---|---|---|---|---|
| | 2.5 | | 5 | | 10 | |
| | MAO-A | MAO-B | MAO-A | MAO-B | MAO-A | MAO-B |
| Cerebellum | 91.7 ± 4.2*# | 61.7 ± 7.0# | 97.6 ± 0.8# | 86.3 ± 1.0# | 98.0 ± 0.6# | 86.9 ± 7.0# |
| Liver | 28.2 ± 11.1 | 1.0 ± 7.1 | 62.6 ± 4.0*# | 4.5 ± 3.6 | 87.5 ± 5.3*# | 31.3 ± 8.2# |
| Intestinum tenue | 56.8 ± 18.0# | 71.3 ± 7.4# | 82.2 ± 7.2# | 73.3 ± 10.5 | 90.7 ± 6.0# | 90.3 ± 3.0# |

FIG.21

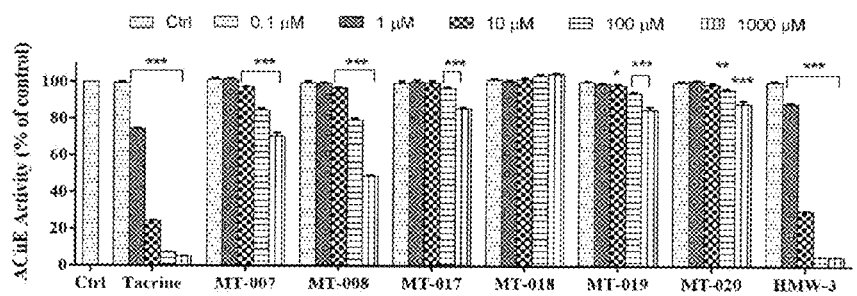
FIG.22
| Compound | Cholinesterase Inhibiting Activity (IC50 µM) | |
|---|---|---|
| | Acetyl Cholinesterase (AChE) | Butyryl Cholinesterase (BuChE) |
| HMW-1 | > 1000 | 185.0 ± 9.3* |
| HMW-2 | 77.8 ± 6.2*# | 5.2 ± 0.4* |
| HMW-3 | 8.3 ± 0.4*# | 3.8 ± 0.3*# |
FIG.23
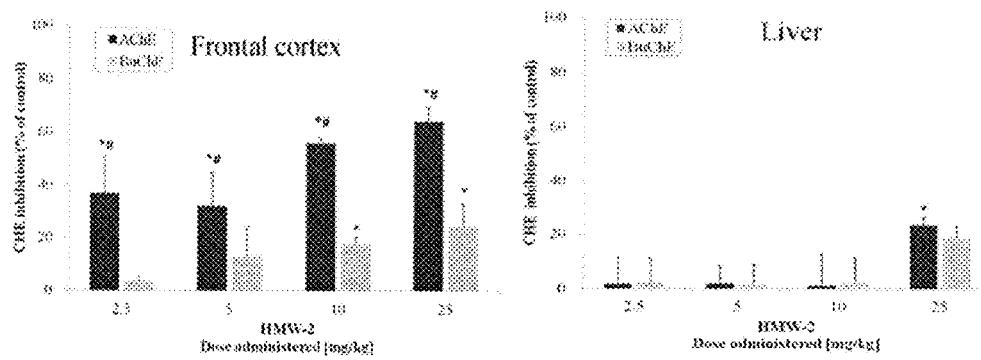
FIG.24

COMPOUNDS WITH NEURAL PROTECTIVE EFFECT, AND PREPARATION AND USE THEREOF

FIELD OF THE INVENTION

The present invention relates to the medical field and, more particularly, to a compound with neural protective effect, and methods for preparation thereof and uses thereof for manufacture of medicaments and for prevention and treatment of diseases.

BACKGROUND OF THE INVENTION

Monoamine oxidases (MAO) are enzymes to catalyze amines in oxidative deamination reaction of monoamines. There are two subtypes of MAO: monoamine oxidase A (MAO-A) and monoamine oxidase B (MAO-B), both of which exist in neurons and astrocytes, but differ in the specificity to substrates and inhibitors. In addition to the central nervous system, MAO-A exists also in liver, gastrointestinal tract and placenta, whereas MAO-B exists mainly in platelets Monoamine oxidases may be an important target of drug action, and a number of drugs have been developed successfully from of the nonoamine oxidases inhibitors. Selective MAO-A inhibitors, such as Clorgiline, can be used for treating depression, and selective MAO-B inhibitors, such as Rasagiline and Selegiline, can be used for treating Parkinson's disease.

In the 1970s, it was found that cholinergic neurotransmitter antagonists can significantly damage the memory function of mice (Deutsch. Science, 1971, 174(4011): 788-794), which indicats that the cholinergic nervous system may play an important role for learning and memory capacity of the brain. Since then, a series of experiments proved that the brain cholinergic system has important effect to consciousness, attention and memory. Cholinesterase becomes an important target of drug action, for instance, acetyl cholinesterase inhibitors (AChEI), mainly through reversible inhibition of acetylcholinesterase, may reduce the speed of acetylcholine degradation and enhance acetylcholine level for improving AD patients' abonormity in memory, thinking, language, judgment, and other brain functions. Currently, the acetyl cholinesterase inhibitors approved by the FDA of the United States for treating AD mainly include Tacrine, Donepezil, Rivastigmine, and Galantamine.

Oxidative stress refers to a condition in physiological processes that the body, when stimulated, produces a large number of oxide intermediates to cause imbalance between reactive oxygen species and antioxidant system. Such imbalances tend to cause excessive generation of free radicals and deminition of the activity of antioxidant system and thus induce the body's oxidative damage. These free radicals include reactive oxygen species (ROS) and reactive nitrogen species (RNS). Free radicals are rather complex in generation, and are closely related to various of physiological and biochemical process (Conrad et al. J Neurochem Int. 2013 April; 62 (5):738-49). Lipid peroxidation may easily occurs as a large amount of polyunsaturated fatty acids exist in the phospholipid bilayer of the neurons, and thus, neuronal cells, as compared to other types of cells, are more susceptible to oxidative stress (Facecchia et al. J Toxicol 2011; 2011, 683-728). Damage of oxygen metabolism to central nervous system may produce more severe oxidative stress effect and further damage of the nervous system (Mohsenzadegan et al. Irfan J Allergy Asthma Immunol, 2012 September; 11 (3):203-16). Under normal conditions, excessive free radicals and reactive oxygen species such as hydrogen peroxide ($H_2O_2$), singlet oxygen and ozone ($O_3$) in the body can be scavenged quickly by antioxidant system, but under pathological conditions, such scavenging activity diminishes. The accumulation of reactive oxygen species may induce nucleic acid fracture, enzymatic inactivation, depolymerization of polysaccharide, and peroxidation of lipids, and eventually lead to neuronal death (Yan et al. Free Radic Biol Med. 2013 September; 62:90-101). There are many factors which can cause oxidative stress, and, for example, $A\beta$, metal ions and mitochondria are considered to play important roles in the process of oxidative stress.

The content of soluble $A\beta$ and hydrogen peroxide production rate show good linear relationship. $A\beta$ can effect the permeability of calcium ion channels, activate NADPH oxidase II(NOX2), make electrons transferred from NADPH to oxygen, increase ROS generation rate, and, at the same time, $A\beta$ has strong affinity metal ions with REDOX activity (Pimentel et al., Oxid Med Cell Longev. 2012; 2012:132-146), after it combined with these active metal ions, it may produce hydrogen peroxide. Studies have shown that prooxidant can promote the formation of $A\beta$, whereas antioxidants, such as vitamin E and some other free radical scavengers, can prevent the damage of $A\beta$ to neurons, and improve cognitive impairment.

Mitochondria is a major site for oxidation-reduction reactions and a major donor of energy in the cells, the free radicals it produced are 90% more than the total amount of free radicals inside the cells, and thus, the normal functions of mitochondria is important to maintain the normal physiological activity (Yan et al. Free Radic Biol Med. 2013, 62:90-101). It has been thought that a variety of neurodegenerative diseases, such as AD, PD, HD, ALS and PSP, are caused mainly from neuron mitochondrial dysfunction (Du et al. Int J Biochem Cell Biol. 2010, 42(5): 560-572). Based on quantitative morphology count of different types of mitochondria (normal, partial damaged or completely damaged) in the brain neurons of AD patients, it is found that as compared with the normal brain neurons of the same age, the content of normal mitochondria in the AD brain neurons decreased significantly, and the content of completely damaged mitochondria increased significantly (Beal et al. Curr Opin Neurobiol. 1996 6(5): 661-6666). The damage of mitochondria induces oxidative damage of neurons, which showed in two expects: one is to cause abnormal function of the electron transport chain (ETC) and make the content of free radicals increased; and the other is to decrease the vitality of mitochondria in antioxidant system through lowering the content of antioxidant small molecules, such as Glutathione, coenzyme Q, vitamin C, vitamin E and enzyme catalysis in the mitochondria.

Existing clinical methods for the treatment of PD are rather limited, and also are merely for temporary alleviation of diseases and not able to stop further attenuation of nerve cells. As there are several different reasons for PD to occur, no satisfied effects could be obtained if only a single-route or single-target administration is given, or the "one-drug and one-target" approach could not be used for fundamental treatment of such diseases. Multifunctional drugs are those having multiple treatment mechanisms for the treatment of a single disease, and many physicians and scientists believed that such multifunctional drugs with multiple functions to multiple targets of a single disease should have greater potential over currently well accepted "one-drug and one-target" approach. The diseases that the multifunctional drugs are used for treatment mainly include difficult and complicated diseases such as depression, schizophrenia, cognitive and movement disorders (Morphy et al. Drug Discov Today. 2004, 9(15): 641-651). Many drugs, however, when used in excess dosage, may show multiple mechanisms not related to the disease itself and thus could induce many side effects, and of course such drugs cannot be considered as multifunctional drugs (Stahl et al. CNS Spectr. 2009, 14(2): 71-73).

Combination drug therapies are often utilized to treat some pathologically complicated diseases, in other words, by using of multiple kinds of drugs which are directed to different targets of a single disease. For instance, human immunodeficiency virus (HIV) reverse transcriptase inhibitors and HIV protease inhibitors are used in combination for the treatment of acquired immune deficiency syndrome (AIDS). Another example is bronchodilator developed for the treatment of inflammation and bronchial asthma, and such drug is a compound preparation from three drug components of fluticasone, corticosteroids and salmeterol, and has been approved by the FDA in the United States. However, combination drug therapy of multiple drug molecules may cause many problems. One of the most important problem is that drug molecules may differ in the properties of such as bioavailability and pharmacokinetic. Even worse, the combination may bring about more toxic or side effects, and different drug molecules may also have interactions. In elderly patients and high risk groups, these side effects may be life threatening. Therefore, the drug research and development on multifunctional drug molecules of "one-drug and multi-targets" approach, which has advantageous of low toxicity, high efficacy, flexible dosage regimen have attracted more and more attention in drug research (Van et al. J Neurochem. 2006, 99(4): 1033-1048).

It is reported that drugs with dual mechanism was developed for treating Alzheimer's disease. Researchers believed that, combination molecules containing both cholinesterase inhibitors and SERT inhibitors can be used to treat AD and at the same time treat the accompanying depression. The use of multi-functional drug compounds with both cholinesterase and SERT inhibiting activities can avoid the side effects caused by excessive undesirable cholinergic stimulation (Toda et al. Bioorg Med Chem. 2003, 11(20): 4389-4415).

SUMMARY OF THE INVENTION

The present invention is directed to compounds having multiple targets and neural protection effect. Based on the pharmacophore concept of drug design, a multiple of pharmacophores with clear target are integrated into a single molecule, so that such molecule has multiple functions of monoamine oxidase inhibiting, cholinesterase inhibiting, free radical scavenging and nerve protection. Such compounds have multiple mechanisms, enhanced medical effects and reduced side effects as compared to combination drugs.

The present invention is also directed to method of preparation of the compound with nerve protective effect.

The present invention is also directed to uses of the compound with nerve protective effect for treatment of diseases and for manufacture of medicaments.

The present invention provides compounds with neural protective effect having a general structure of formula (I) below:

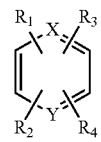
(I)

wherein:
X and Y are each independently C or N;
$R_1$, $R_2$, $R_3$, $R_4$ are each independently H, alkyl, ester group, optionally substituted urethane group, nitronyl group or propargyl amino group; any two adjacent substituents of $R_1$, $R_2$, $R_3$ and $R_4$ can be linked to form a ring structure; and $R_1$, $R_2$, $R_3$ and $R_4$ contain at least two different groups selected from substituted or unsubstituted urethane group, nitronyl group and propargyl amino group.

The compounds of formula (I), in preferred embodiments, have a general structure of formula (II):

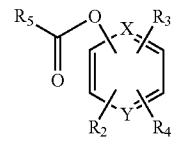
(II)

wherein:
X and Y are each independently C or N;
$R_2$, $R_3$, $R_4$ are each independently H, alkyl, ester group, optionally substituted urethane group, nitronyl group or propargyl amino group; any two adjacent substituents of $R_2$, $R_3$ and $R_4$ can be linked to form a ring structure; and at least one of $R_2$, $R_3$ and $R_4$ is selected from substituted or unsubstituted urethane group, nitronyl group and propargyl amino group; and
$R_5$ is substituted or unsubstituted amino, alkyl, aryl or heteroaryl group.

The compounds, in further preferred embodiments, have a general structure of formula (III):

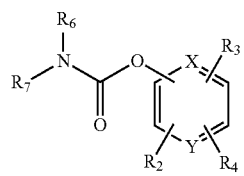
(III)

wherein: $R_6$ and $R_7$ are each independently hydrogen or alkyl. For example, the alkyl is C1-C5 alkyl.

The compounds of formula (I), in further preferred embodiments, have a general structure of formula (IV):

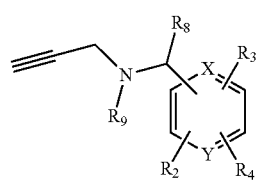
(IV)

wherein:

$R_2$, $R_3$ and $R_4$ are each independently hydrogen, alkyl, ester group, or substituted or unsubstituted urethane group, nitronyl group or propargyl amino group; and at least one of $R_2$, $R_3$ and $R_4$ is selected from substituted or unsubstituted urethane group, nitronyl group and propargyl amino group; and $R_8$ and $R_9$ are each independently hydrogen, methyl, ethyl or propargyl group, wherein $R_8$ can also be linked with $R_2$, $R_3$ or $R_4$ to form a ring structure.

The compounds of formula (II), in preferred embodiments, have a general structure of formula (V):

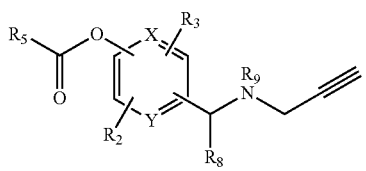

(V)

wherein:

X and Y are each independently C or N;

$R_2$ and $R_3$ are each independently hydrogen, alkyl, ester group, or substituted or unsubstituted urethane group, nitronyl group or propargyl amino group;

$R_5$ is substituted or unsubstituted amino, alkyl, aryl or heteroaryl group; and $R_8$ and $R_9$ are each independently hydrogen, methyl, ethyl or propargyl group, wherein $R_8$ can also be linked with $R_2$, or $R_3$ to form a ring structure.

The compounds of formula (II), in preferred embodiments, have a general structure of formula (VI):

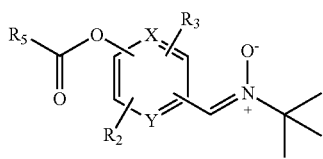

(VI)

wherein:

X and Y are each independently C or N;

$R_2$ and $R_3$ are each independently hydrogen, alkyl, ester group, or substituted or unsubstituted urethane group, nitronyl group or propargyl amino group; and $R_5$ is substituted or unsubstituted amino, alkyl, aryl or heteroaryl group.

The compounds of formula (III), in further preferred embodiments, have a general structure of formula (VII):

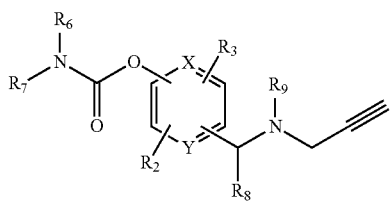

(VII)

wherein: $R_2$ and $R_3$ are each independently hydrogen or alkyl. For example, the alkyl is C1-C5 alkyl.

The compounds of formula (VI), in further preferred embodiments, have a general structure of formula (VIII):

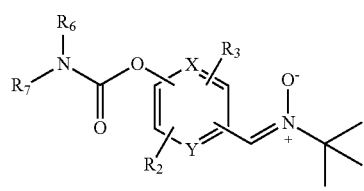

(VIII)

wherein: $R_6$ and $R_7$ are each independently hydrogen or alkyl. For example, the alkyl is C1-C5 alkyl.

The compounds of formula (I), in further preferred embodiments, have a general structure of formula (IX):

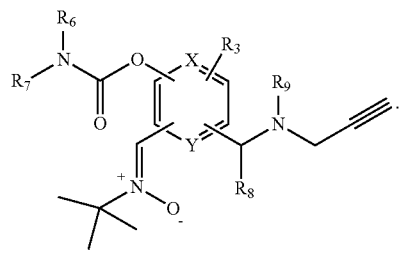

(IX)

wherein:

$R_3$ is hydrogen, alkyl, ester group, or substituted or unsubstituted urethane group, nitronyl group or propargyl amino group;

$R_5$ is substituted or unsubstituted amino, alkyl, aryl or heteroaryl group; and $R_8$ and $R_9$ are each independently hydrogen, methyl, ethyl or propargyl group, wherein $R_8$ can also be linked with $R_3$ to form a ring structure.

The compounds of formula (IX), in further preferred embodiments, have a general structure of formula (X):

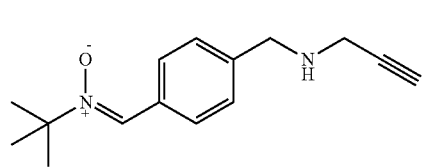

(X)

wherein: $R_6$ and $R_7$ are each independently hydrogen or alkyl. For example, the alkyl is C1-C5 alkyl.

The compounds of formula (I), in further preferred embodiments, are selected from, but not limited to, the group below:

MT-002

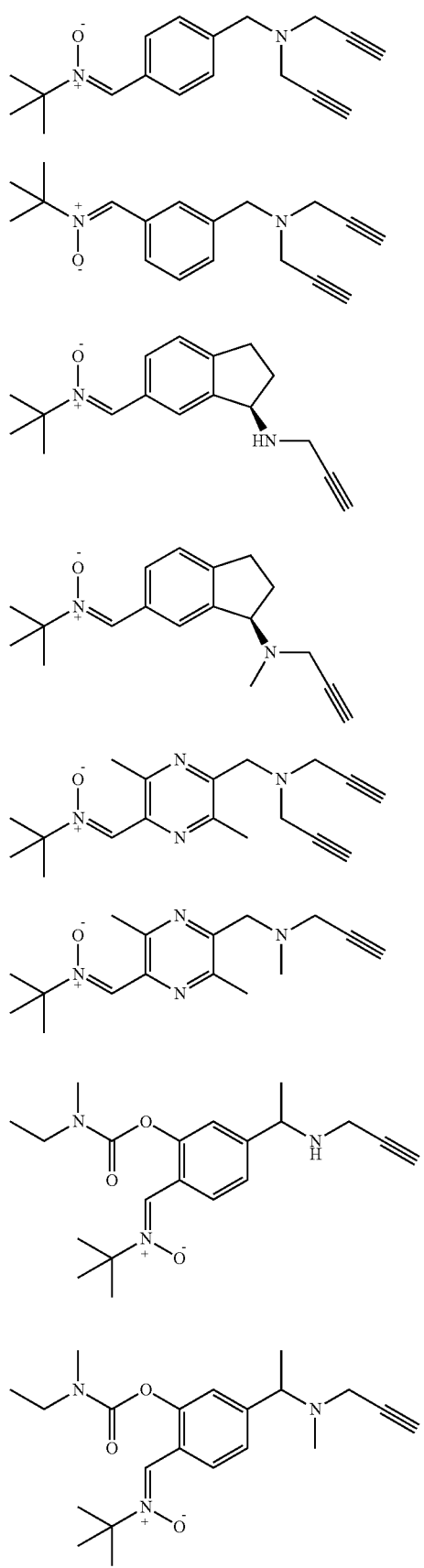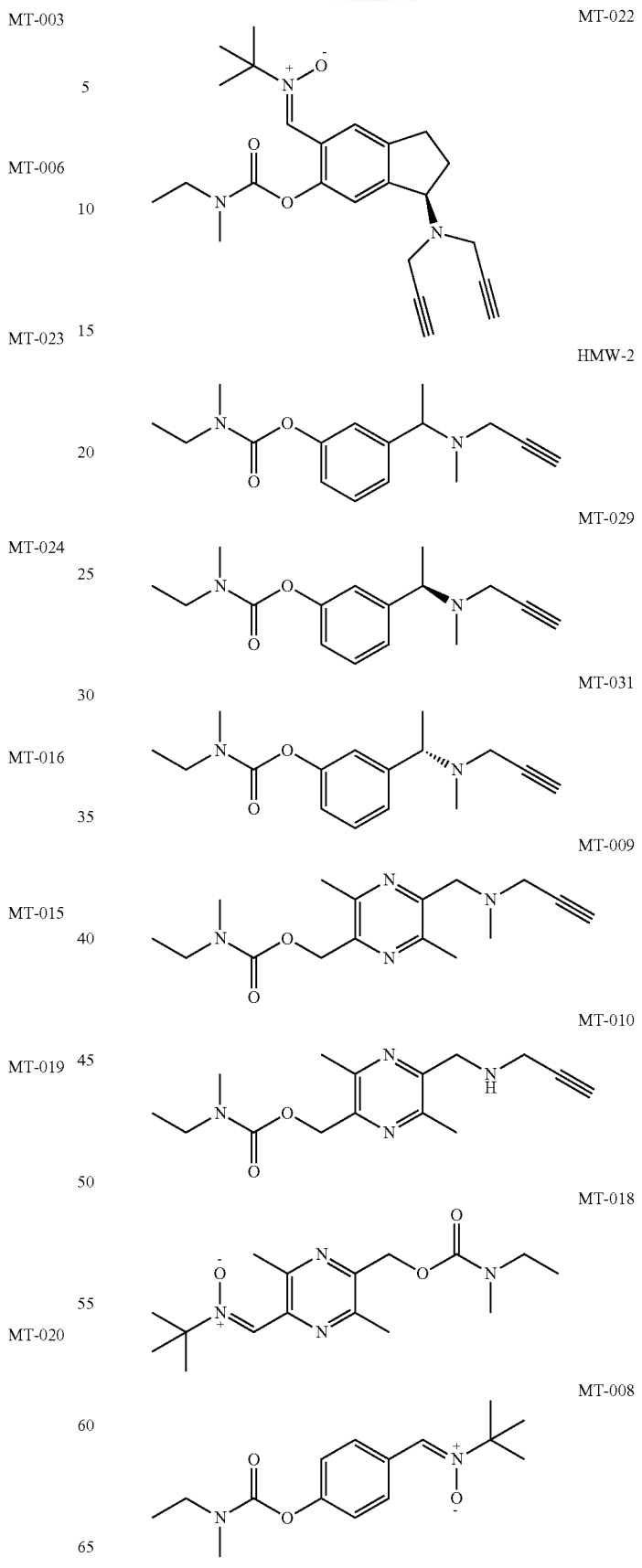

The compounds of the present invention have protective effect to cells especially nerve cells, and can be used for manufacture of medicaments for protection of cells. Such medicaments may include a pharmaceutically effective amount of the compounds of formula (I) or pharmaceutically acceptable salts thereof to be taken by patients.

The compounds of the present invention have multiple mechanisms or functions, including for example, as inhibitor of monoamine oxidase and cholinesterase, scavenger of free radicals, and protection of cells such as nerve cells, and thus the medicaments manufactured from such compounds may be used to prevent or treat monoamine oxidase, cholinesterase and free radicals related diseases, including: neurodegeneration related diseases, such as Alzheimer's disease, Parkinson's disease and stroke, and free radical related diseases, such as heart disease and diabetes.

The present invention further provides a method for the prevention or treatment of the above-mentioned diseases. Such method includes administering to a patient a drug manufactured from the compounds of this invention, including an effective amount of a compound of formulae (I) to (X) or a pharmaceutically acceptable salt thereof or a pharmaceutical composition thereof.

The following definitions are set forth to illustrate and define the meaning and scope of the various terms used to describe the invention herein.

As used herein, the term "alkyl" refers to unsubstituted or substituted linear, branched or cyclic alkyl carbon chains of up to 10 carbon atoms. Such linear alkyl groups include, for example, methyl, ethyl, n-propyl, n-butyl, n-pentyl, n-hexyl, n-heptyl and n-octyl. Such branched alkyl groups include, for example, iso-propyl, sec-butyl, iso-butyl, tert-butyl and neopentyl. Such cyclic alkyl ("cycloalkyl") groups include, for example, cyclopropyl, cyclobutyl, cyclopentyl and cyclohexyl. The alkyl groups can be substituted with one or more substituents. Non-limiting examples of such substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl. The term "alkyl" also refers to unsubstituted or substituted linear, branched or cyclic chains of up to 10 carbon atoms that contain at least one heteroatom (e.g., nitrogen, oxygen or sulfur) in the chain. Such linear alkyl groups include, for example, $CH_2CH_2OCH_3$, $CH_2CH_2N(CH_3)_2$ and $CH_2CH_2SCH_3$. The branched groups include, for example, $CH_2CH(OCH_3)CH_3$, $CH_2CH(N(CH_3)_2)CH_3$ and $CH_2CH(OCH_3)CH_3$. Such cyclic alkyl groups include, for example, six-membered $CH(CH_2CH_2)_2O$, $H(CH_2CH_2)_2NCH_3$, $CH(CH_2CH_2)_2S$, and corresponding five-membered groups. Such alkyl groups can be substituted with one or more substituents. Non-limiting examples of such substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl.

As used herein, the term "aryl" refers to an unsubstituted or substituted aromatic, carbocyclic, and heteroaryl groups. Aryl groups are either single ring or multiple condensed ring compounds. A phenyl group, for example, is a single ring aryl group. A naphthyl group exemplifies an aryl group with multiple condensed rings. Aryl groups can be substituted with one or more substituents. Non-limiting examples of such substituents include $NH_2$, $NO_2$, $N(CH_3)_2$, $ONO_2$, F, Cl, Br, I, OH, $OCH_3$, $CO_2H$, $CO_2CH_3$, CN, aryl and heteroaryl.

As used herein, the term "heteroaryl" refers to an unsubstituted or substituted aromatic mono- or poly-cyclic group containing at least one heteroatom within a ring, e.g., nitrogen, oxygen or sulfur. For example, typical heteroaryl groups with one or more nitrogen atoms include tetrazoyl, pyrrolyl, pyridyl (e.g., 4-pyridyl, 3-pyridyl, 2-pyridyl), pyridazinyl, indolyl, quinolyl (e.g., 2-quinolyl, 3-quinolyl), imidazolyl, isoquinolyl, pyrazolyl, pyrazinyl, pyrimidinyl, pyridonyl or pyridazinonyl; typical oxygen heteroaryl groups with an oxygen atom include 2-furyl, 3-furyl or benzofuranyl; typical sulfur heteroaryl groups are thienyl, and benzothienyl; typical mixed heteroatom heteroaryl groups include furazanyl, oxazolyl, isoxazolyl, thiazolyl, and phenothiazinyl. The heteroaryl groups can be substituted with one or more substituents. Non-limiting examples of such substituents include $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl and heteroaryl. Further, the term also includes instances where a heteroatom within the ring has been oxidized, for example, to form an N-oxide, ketone or sulfone.

As used herein, the term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described below, and, at length by E. W. Martin, in Remington's Pharmaceutical Sciences, Mack Publishing Company (1995), Philadelphia, Pa., $19^{th}$ ed.

The new compounds herein include those of formulae (I) to (X). The compounds contain at least two different groups selected from substituted or unsubstituted nitronyl group, propargyl amino group, and ester group (including urethane group). These compounds have multiple functions, including inhibition of monoamine oxidase and cholinesterase, scavenging of free radicals, and protection of cells especially never cells, and thus can be used for manufacture of medicaments for cell protection, to prevent or treat monoamine oxidase, cholinesterase and free radicals related diseases, usually including: neurodegeneration related diseases and free radical related diseases. Such diseases include but not limited to: monoamine oxidase related diseases, such as Parkinson's disease, Alzheimer's disease, hypertension, diarrhea, depression, asthma, and allergies; cholinesterase related diseases, such as Alzheimer's disease, Parkinson's disease, Huntington's, amyotrophic lateral sclerosis, myasthenia gravis, and glaucoma, thyroid function hyperfunction, hypertension, bronchial asthma, type IV high lipoprotein hematic disease, kidney failure; oxidative stress injury and free radicals related diseases, such as stroke, brain trauma, epilepsy, Parkinson's disease, Huntington's disease, amyotrophic lateral sclerosis, Alzheimer's disease, hypoxic ischemic brain damage, cerebral hemorrhage, ischemic heart disease, vascular thrombosis, atherosclerosis, hypercholesterolemia, emphysema, cataract, diabetes mellitus, acute pancreatitis, alcoholic liver disease, kidney damage, and cancer; and neurodegenerative diseases, such as cerebral ischemia, Parkinson's disease, Alzheimer's disease, amyotrophic lateral sclerosis, ataxia, capillaries expansion of bovine spongiform encephalopathy, creutzfeldt-jakob disease, Huntington's disease, cerebellum atrophy, multiple sclerosis, primary amyotrophic lateral sclerosis, and spinal muscular atrophy.

The compounds of the present invention and derivatives thereof contain ester group (including substituted or unsubstituted substituted or unsubstituted urethane group), nitronyl group or propargyl amino group, and can be administered to patients in the form of a pharmaceutically acceptable salt or a pharmaceutical complex. Certain complex may need to form a pharmaceutical composition with a suitable carrier or excipient. The term "therapeutically effective amount" refers to an amount of the compounds that is necessary to achieve a desired effect.

A variety of preparations can be used to formulate pharmaceutical compositions containing the compounds with multiple functions of mechanisms, including solid, semi solid, liquid and gaseous forms (*Remington's Pharmaceutical Sciences*, Mack Publishing Company (1995), Philadelphia, Pa., 19$^{th}$ ed). Tablets, pills, granules, dragees, gels, slurries, ointments, solutions, suppositories, injections, inhalants and aerosols are examples of such formulations. The formulations can be administered in either a local or systemic manner or in a depot or sustained release fashion. Administration of the composition can be performed in a variety of ways. Among others, oral, buccal, rectal, parenteral, intraperitoneal, intradermal, transdermal and intratracheal means can be used.

The compounds described herein are given by injection, they can be formulated by dissolving, suspending or emulsifying it in an aqueous or nonaqueous solvent. Vegetable or similar oils, synthetic aliphatic acid glycerides, esters of higher aliphatic acids and propylene glycol are examples of nonaqueous solvents. The compound is preferably formulated in aqueous solutions such as Hank's solution, Ringer's solution or physiological saline buffer.

The compounds described herein are given orally, they can be formulated through combination with pharmaceutically acceptable carriers that are known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxypropylmethyl-cellulose, sodium carboxymethylcellulose and polyvinylpyrrolidone (PVP).

The compounds described herein are can also be delivered in an aerosol spray preparation from a pressurized pack and a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Pharmaceutical compositions according to the present invention contain a therapeutically effective amount of the compounds of multiple mechanisms. The amount of the compound will depend on the patient being treated. The patient's weight, severity of illness, manner of administration and judgment of the prescribing physician should be taken into account in deciding the proper amount. The determination of a therapeutically effective amount of the compounds described herein should be made by an experienced physician.

Although a therapeutically effective amount of the compound described herein or its derivative will vary according to the patient being treated, suitable doses will typically be in the range between about 10 mg and 10 g of the compound.

The present invention has the advantages over prior art: the present invention provides substances with novel structures and multiple mechanisms or functions, and such substances can be used for inhibition of monoamine oxidase and cholinesterase, scavenging of free radicals, and protection of cells especially never cells, and thus can be used for manufacture of medicaments for cell protection, to prevent or treat monoamine oxidase, cholinesterase and free radicals related diseases, usually including: neurodegeneration related diseases, such as Alzheimer's disease, Parkinson's disease and stroke, and free radical related diseases, such as heart disease and diabetes.

BRIEF DESCRIPTION OF THE DRAWINGS

FIG. 1 is a scheme of exemplary Synthesis of compounds of MT-001, MT-002 and MT-003.

FIG. 2 is a scheme of exemplary Synthesis of compounds of MT-004, MT-005 and MT-006.

FIG. 13 is a scheme of exemplary Synthesis of compounds of MT-026 and MT-027.

FIG. 14 is a scheme of exemplary Synthesis of compounds of MT-028 and MT-029.

FIG. 19, in accordance to an embodiment of the present invention, illustrates MAO-A/B inhibiting activity of the compounds.

FIG. 20, in accordance to an embodiment of the present invention, illustrates MAO-A/B inhibiting activity (1 hour) of the compound of 5 mg/kg HMW-2.

FIG. 21, in accordance to an embodiment of the present invention, illustrates MAO-A/B inhibiting activity (2 hours) of the compound of HMW-2.

FIG. 22, in accordance to an embodiment of the present invention, illustrates in vitro acetylcholin esterase (AChE) inhibiting effect of the compounds.

FIG. 23, in accordance to an embodiment of the present invention, illustrates in vitro acetylcholin esterase (AChE) and butyrylcholine esterase (BuChE) inhibiting effect of the compounds.

FIG. 24, in accordance to an embodiment of the present invention, illustrates in vivo acetylcholin esterase (AChE) and butyrylcholine esterase (BuChE) inhibiting effect of the compound of HMW-2.

DETAILED DESCRIPTION OF THE EMBODIMENTS

Figure 3:
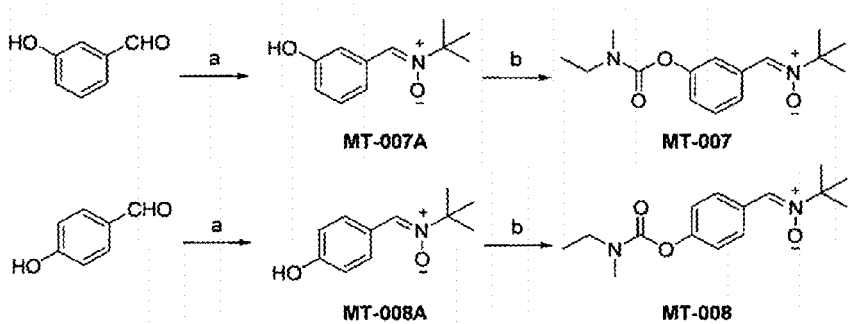
FIG. 3 is a scheme of exemplary Synthesis of compounds of MT-007 and MT-008.
Figure 4:
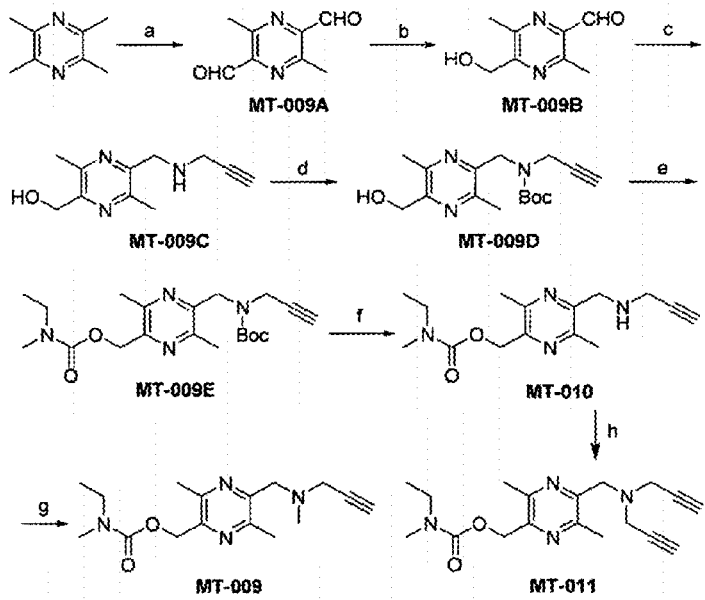
FIG. 4 is a scheme of exemplary Synthesis of compounds of MT-009, MT-010 and MT-011.
Figure 5:
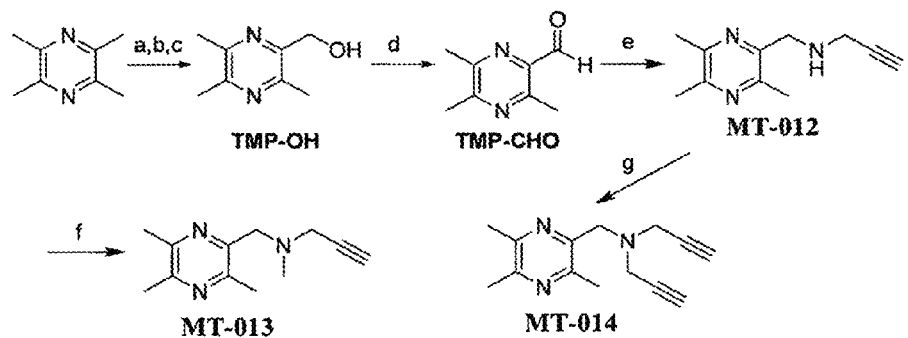
FIG. 5 is a scheme of exemplary Synthesis of compounds of MT-012, MT-012 and MT-014.
Figure 6:
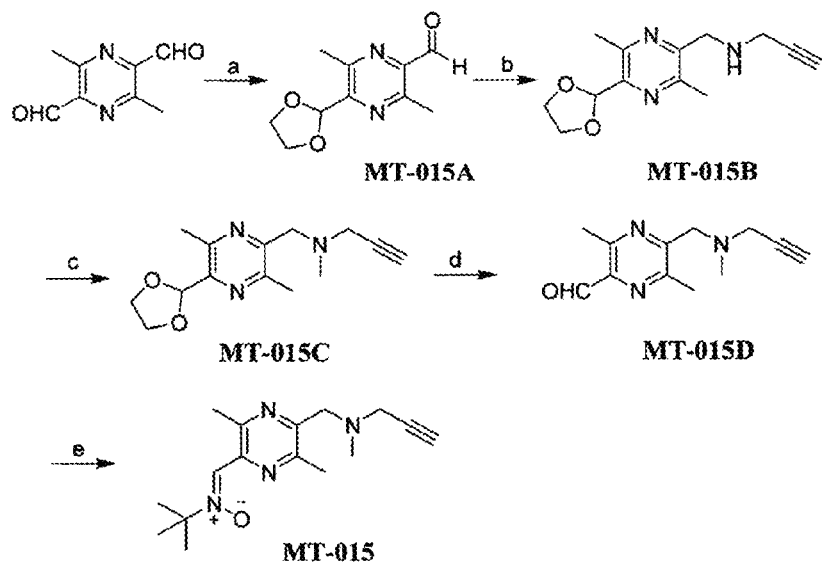
FIG. 6 is a scheme of exemplary Synthesis of compounds of MT-015.
Figure 7:
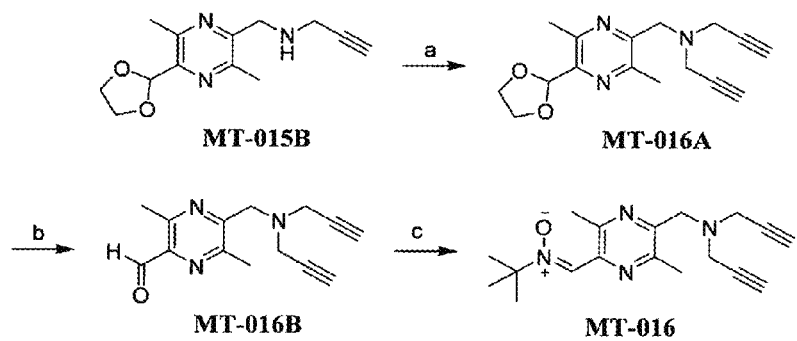
FIG. 7 is a scheme of exemplary Synthesis of compound of MT-016.
Figure 8:
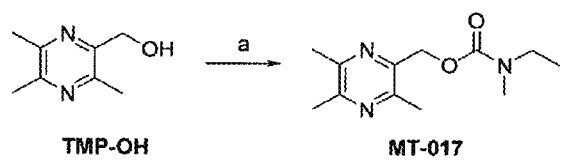
FIG. 8 is a scheme of exemplary Synthesis of compound of MT-017.
Figure 9:
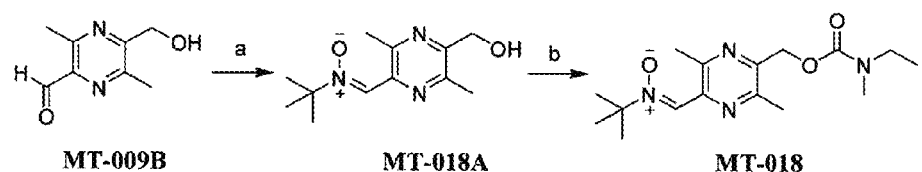
FIG. 9 is a scheme of exemplary Synthesis of compound of MT-018.
Figure 10:
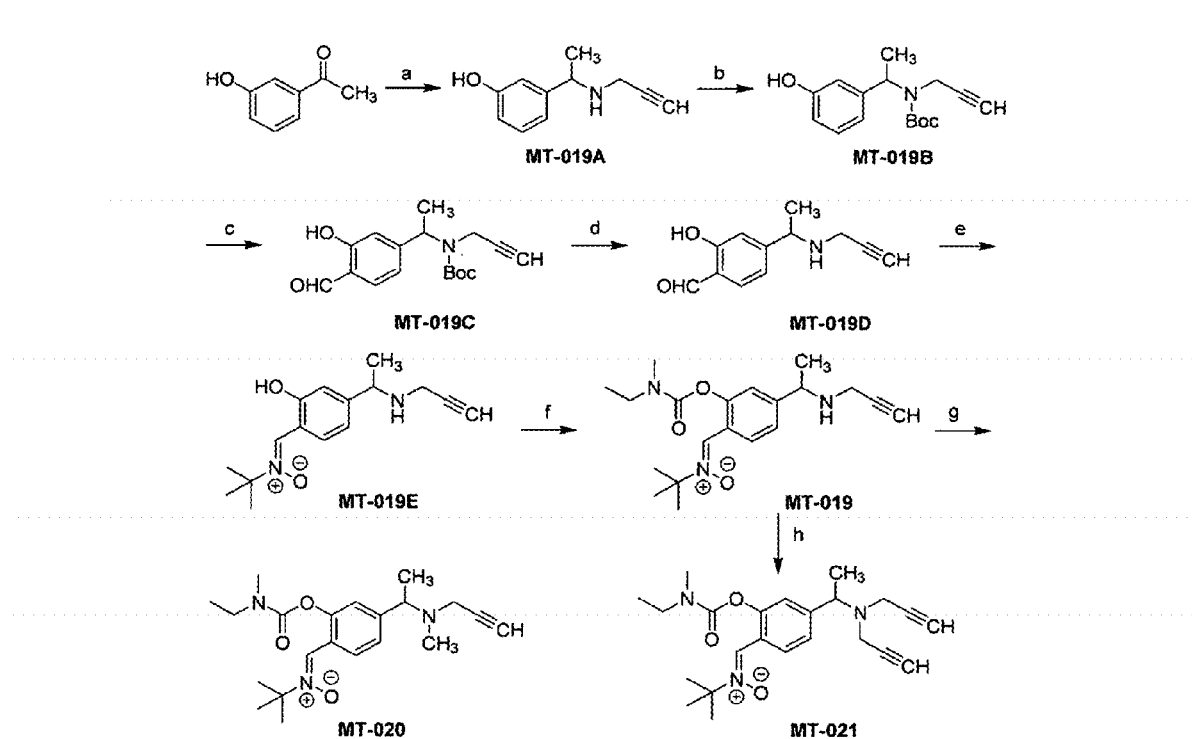
FIG. 10 is a scheme of exemplary Synthesis of compounds of MT-019 and MT-020, MT-021.
Figure 11:
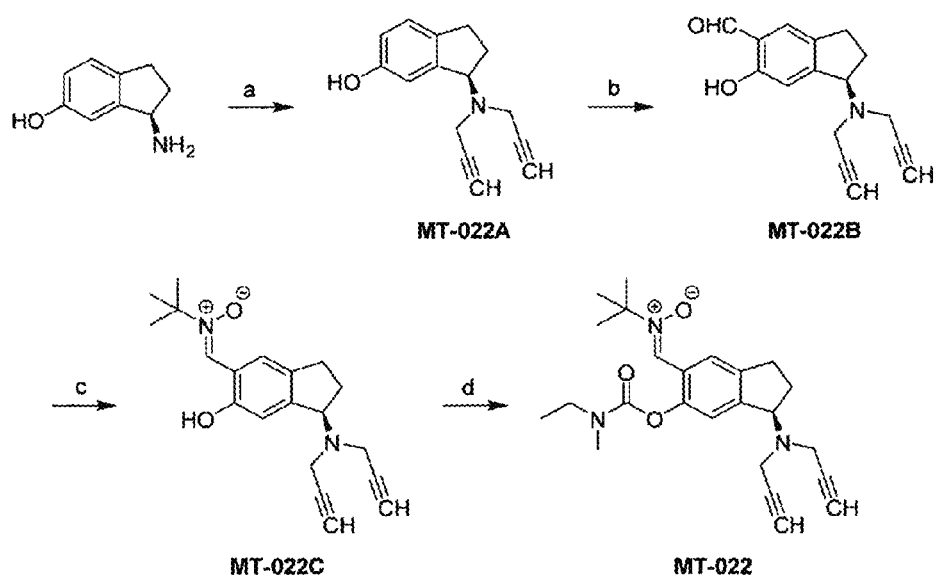
FIG. 11 is a scheme of exemplary Synthesis of compound of MT-022.
Figure 12:
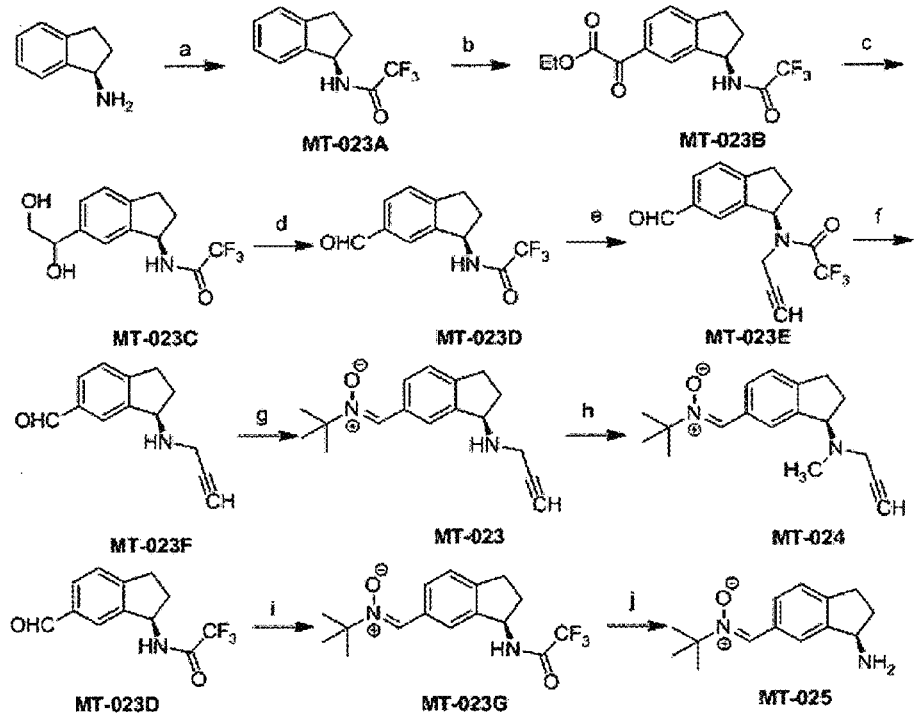
FIG. 12 is a scheme of exemplary Synthesis of compounds of MT-023 and MT-024, MT-025.
Figure 15:
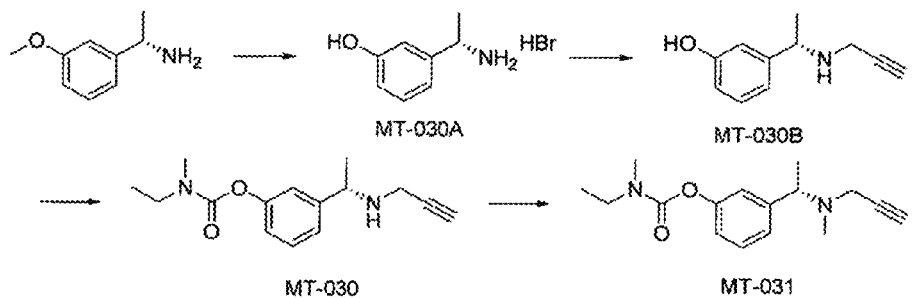
FIG. 15 is a scheme of exemplary Synthesis of compounds of MT-030 and MT-031.
Figure 16:
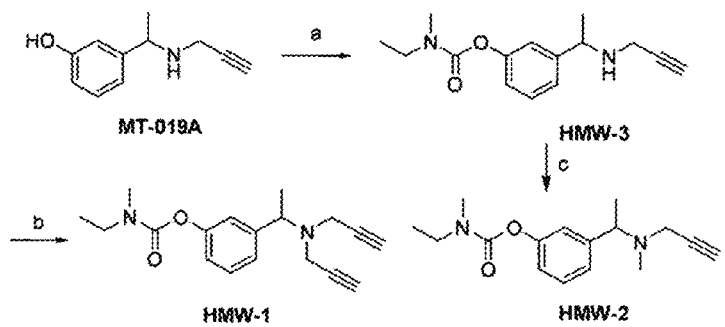
FIG. 16 is a scheme of exemplary Synthesis of compounds of HMW-1, HMW-2 and HMW-3.
Figure 17A:
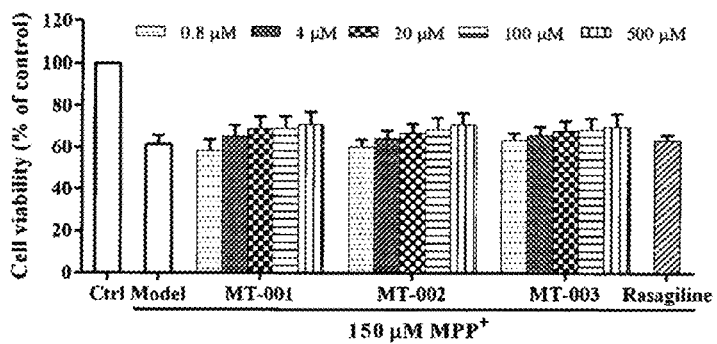
FIGS. 17A to 17I, in accordance to an embodiment of the present invention, illustrate the protective effect of the compounds to MPP$^+$ induced damage of cerebellar granule cells.
Figure 17B:
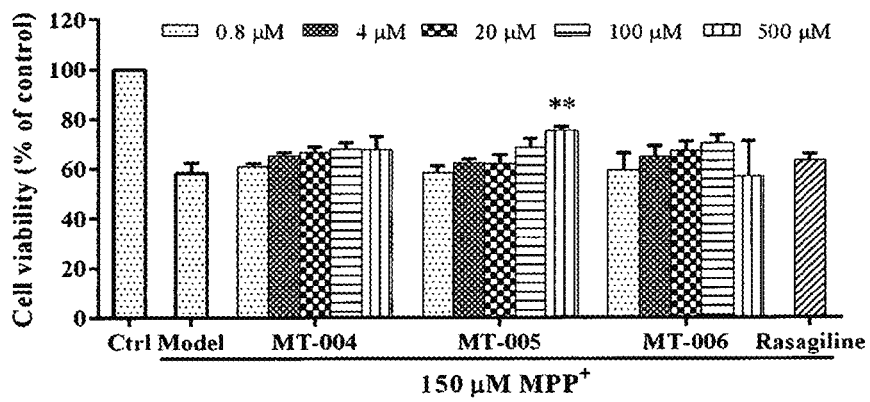
Figure 17C:
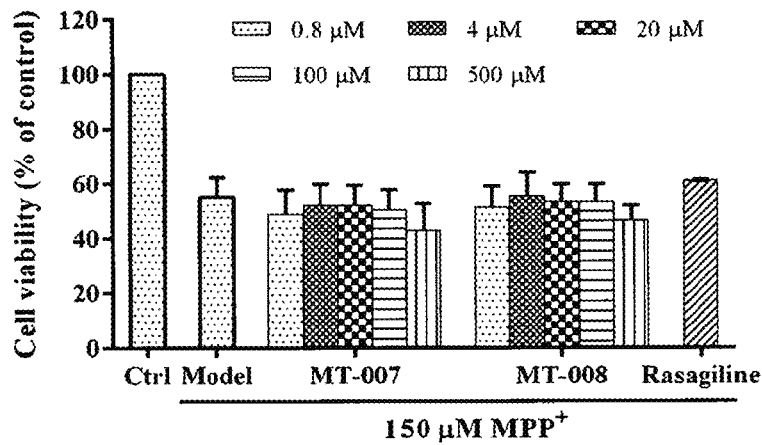
Figure 17D:
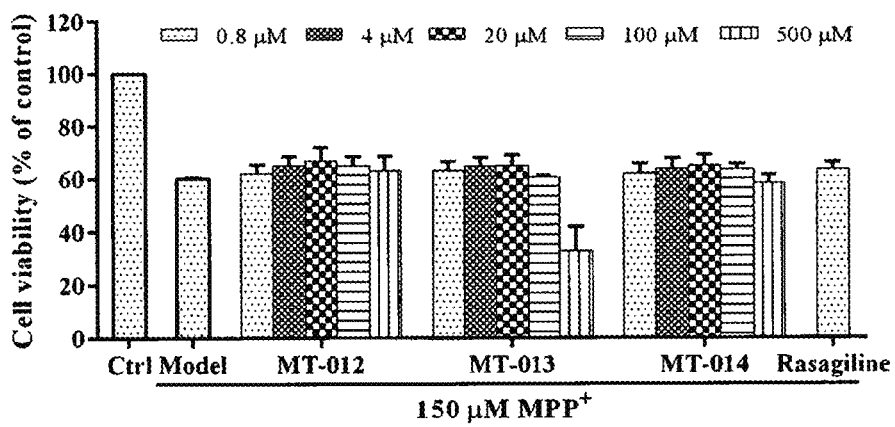
Figure 17E:
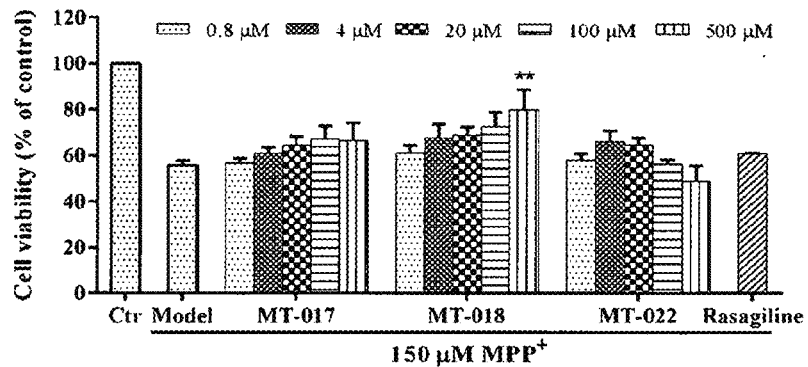
Figure 17F:
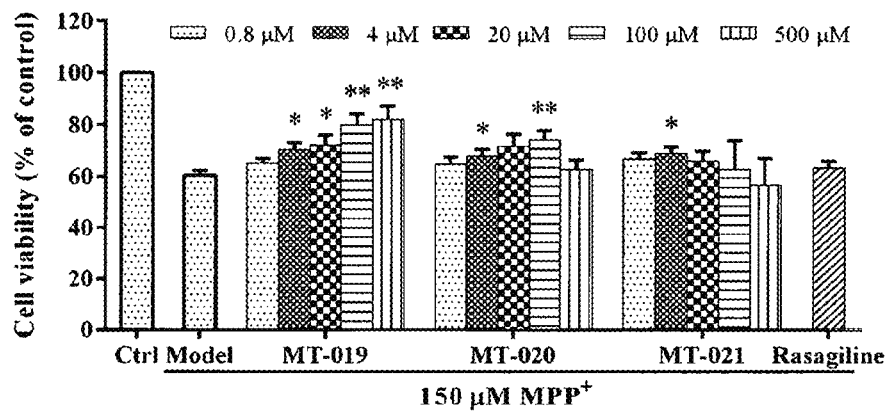
Figure 17G:
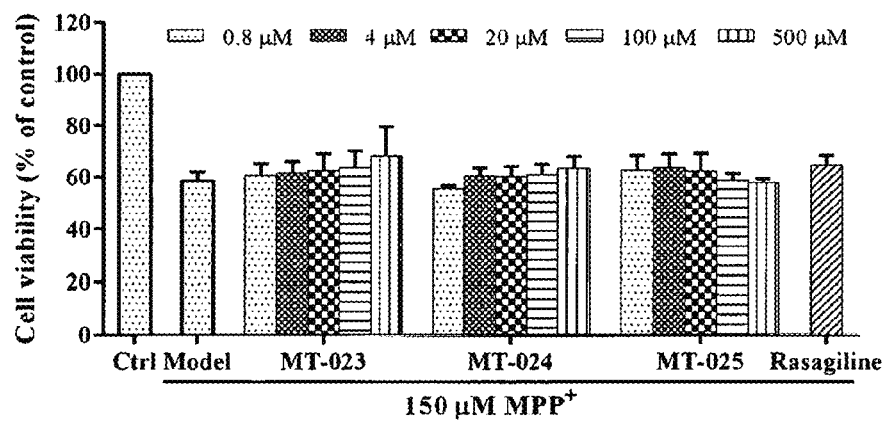
Figure 17H:
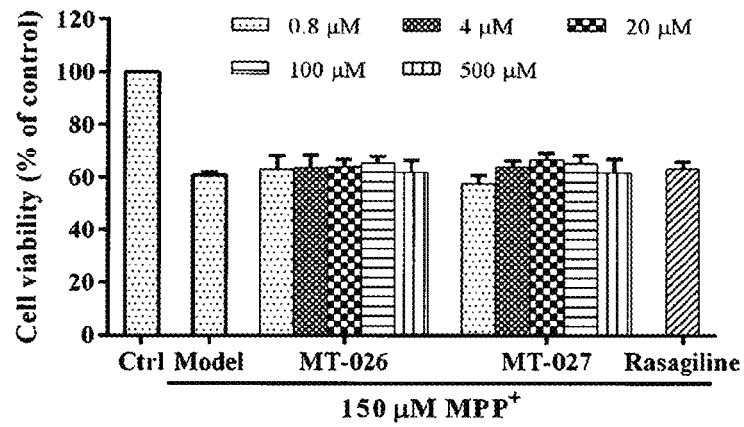
Figure 17I:
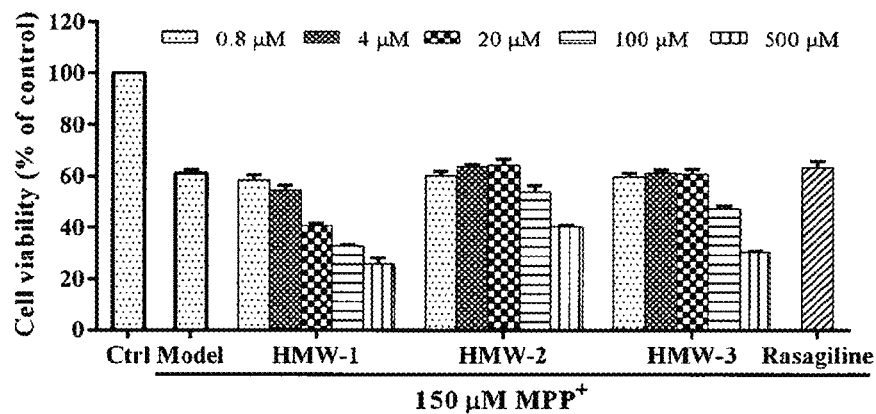
Figure 18:
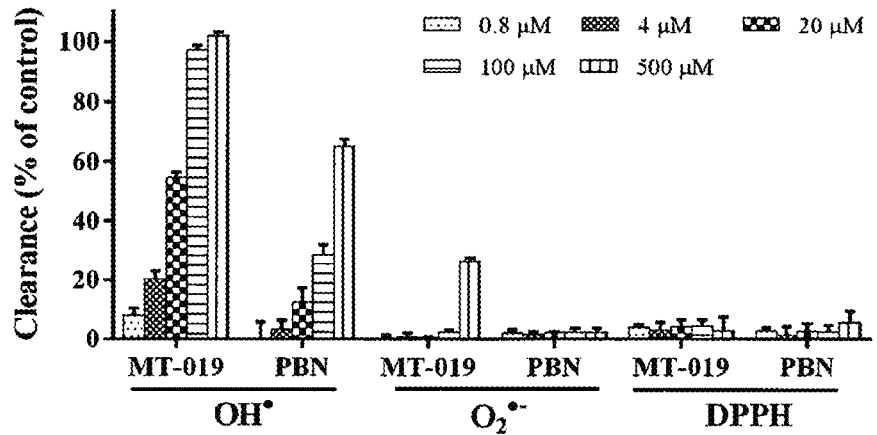
FIG. 18, in accordance to an embodiment of the present invention, illustrates free radical scavenging effect of the compounds.
Figure 25:
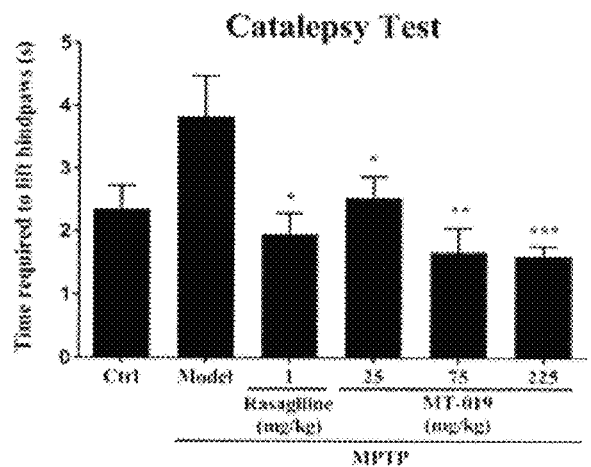
FIG. 25, in accordance to an embodiment of the present invention, illustrates the recovery effect of the compound of MT-019 to behavioral abnormalities in MPTP induced Parkinson's disease (PD) mouse models.

The following examples are intended for illustration only and are not intended to restrict the scope of the present invention in any way.

Example 1. Synthesis of Compound MT-011A p-Phthalaldehyde (1.34 g, 10 mmol) was dissolved in 25 mL of methanol, concentrated hydrochloric acid (1.5 mL) and propargylamine (0.66 g, 12 mmol) were added separately at room temperature, the solution was stirred for 10 min and NaBH$_3$CN (1.26 g, 20 mmol) was added, and the reaction was heated to 68° C. and refluxed for 3 hours. The reaction was followed by TLC, solvent was evaporated after completion of the reaction, 20 mL of water was added, extracted 3 times with ethyl acetate (25 mL×3), the organic layers were combined and dried over anhydrous Na$_2$SO$_4$, then the solvent was evaporated under reduced pressure, the resulting material was separated with silica gel column (ethyl acetate:petroleum ether=1:3) to give the compound MT-001A as a colorless oil (1.7 g, 78%). ESI-MS: [M+H]$^+$ m/z 220.4. $^1$H-NMR (CDCl$_3$, 300 MHz) δ: 1.60 (s, 1H), 2.27 (t, J=2.4 Hz, 1H), 3.32 (s, 6H), 3.41 (d, J=2.4 Hz, 2H), 3.88 (s, 2H), 5.38 (s, 1H), 7.33 (m, 2H), 7.41 (m, 2H).

Example 2. Synthesis of Compound MT-001B

Compound MT-001A (0.5 g, 2.3 mmol) was dissolved in a solution of mixture of HCl:H$_2$O:THF=1:6:7 (12 mL), the reaction was run at room temperature for 12 hours and monitored by TLC. After the reaction was complete, an aqueous solution of K$_2$CO$_3$ was added to adjust pH to neutral, extracted 3 times with ethyl acetate (15 mL×3), the organic layers were combined and dried over anhydrous Na$_2$SO$_4$, and passed through with anhydrous HCl gas, and a white solid was precipitated, allowed to stay for 1 hour, and filtered to give the compound MT-001B as a white solid (0.41 g, 86%). ESI-MS: [M+H]$^+$ m/z 174.0. $^1$H-NMR (DMSO-d6, 300 MHz) δ: 3.30 (s, 1H), 3.76 (m, 1H), 3.89 (d, J=15 Hz, 2H), 4.22 (d, J=36 Hz, 2H), 4.43 (s, 1H), 7.37 (d, J=8.1 Hz, 1H), 7.51 (d, J=8.1 Hz, 1H), 7.77 (d, J=8.1 Hz, 1H), 7.97 (d, J=8.1 Hz, 1H), 10.05 (s, 1H).

Example 3. Synthesis of Compound MT-002

Compound MT-001B (0.25 g, 1.2 mmol) was taken, and an aqueous solution of NaHCO$_3$ was added to adjust pH to neutral, then extracted with ethyl acetate, spin-dried, added to 25 mL of ethanol, then t-butyl hydroxylamine (0.2 g, 2.4 mmol) was added, and the reaction was run at room temperature for 8 and monitored by TLC. After the reaction was complete, the solvent was evaporated to dryness under reduced pressure, the resulting material was separated with silica gel column chromatography (ethyl acetate:petroleum ether=1:1) to give the compound MT-002 as a white solid (0.17 g, 57%). ESI-MS: [M+H]$^+$ m/z 245.2. $^1$H-NMR (DMSO-d6, 300 MHz) δ: 1.50 (s, 9H), 1.99 (s, 1H), 3.09 (t, J=2.4 Hz, 1H), 3.28 (d, J=2.4 Hz, 2H), 3.76 (s, 2H), 7.36 (d, J=8.1 Hz, 2H), 7.81 (s, 1H), 8.30 (d, J=8.1 Hz, 2H).

Example 4. Synthesis of Compound MT-001

Compound MT-002 (0.37 g, 1.5 mmol) was dissolved in 30 mL of acetonitrile, NaHCO$_3$ (0.13 g, 1.5 mmol) and CH$_3$I (0.21 g, 1.5 mmol) were separately added, and the reaction was run at room temperature for 2 hours and followed by TLC, after the reaction was complete, solvent was evaporated, water was added and extracted 3 times with ethyl acetate (20 mL×3), the organic layers were combined and dried over anhydrous Na$_2$SO$_4$, then the solvent was evaporated under reduced pressure, the resulting material was separated with silica gel column chromatography (ethyl acetate:petroleum ether=1:2) to give the compound MT-001 as a colorless oil (0.23 g, 60%). ESI-MS: [M+H]$^+$ m/z 259.4. $^1$H-NMR (CDCl$_3$, 300 MHz) δ: 1.63 (s, 9H), 2.29 (t, J=2.4 Hz, 1H), 2.35 (s, 3H), 3.32 (d, J=2.4 Hz, 2H), 3.62 (s, 2H), 7.42 (d, J=8.4 Hz, 2H), 7.56 (s, 1H), 8.27 (d, J=8.4 Hz, 2H).

Example 5. Synthesis of Compound MT-003

Compound MT-002 (0.37 g, 1.5 mmol) was dissolved in methanol (30 mL), NaHCO$_3$ (0.13 g, 1.5 mmol) and propargyl bromide (0.18 g, 1.5 mmol) were added respectively, the reaction was refluxed for 2 hours and monitored by TLC, after the reaction was complete, solvent was evaporated, water was added and extracted 3 times with ethyl acetate (20 mL×3), the organic layers were combined and dried over anhydrous Na$_2$SO$_4$, then the solvent was evaporated under reduced pressure, and the resulting material was separated with silica gel column chromatography (ethyl acetate:petroleum ether=1:3) to give the compound MY-003 as a white solid (0.29 g, 68%) was obtained. ESI-MS: [M+H]$^+$ m/z 283.1. $^1$H-NMR (DMSO-d6, 300 MHz) δ: 1.50 (s, 9H), 3.21 (t, J=2.4 Hz, 2H), 3.33 (d, J=2.4 Hz, 4H), 3.63 (s, 2H), 7.34 (d, J=8.4 Hz, 2H), 7.83 (s, 1H), 8.33 (d, J=8.4 Hz, 2H).

Example 6. Synthesis of Compound MT-004A m-Phthalaldehyde (1.34 g, 10 mmol) was dissolved in 25 mL of methanol, concentrated hydrochloric acid (1.5 mL) and propargyl amine (0.66 g, 12 mmol) were added respectively at room temperature, the reaction was stirred for 10 min, then NaBH$_3$CN (1.26 g, 20 mmol) was added, heated up to 68° C., and monitored by TLC, after the reaction was complete, the solvent was evaporated, water (20 mL) was added, and extracted three times with ethyl acetate (25 mL×3), the organic layers were combined and dried over anhydrous Na$_2$SO$_4$, the solvent was evaporated under reduced pressure, and the resulting material was separated with silica gel column chromatography (ethyl acetate:petroleum ether=1:3) to give the compound MT-004A as a colorless oil (1.4 g, 65%). ESI-MS: [M+H]$^+$ m/z 220.2. $^1$H-NMR (CDCl$_3$, 300 MHz) δ: 1.95 (s, 1H), 2.27 (t, J=2.4 Hz, 1H), 3.33 (s, 6H), 3.41 (d, J=2.4 Hz, 2H), 3.88 (s, 2H), 5.38 (s, 1H), 7.33 (m, 3H), 7.43 (s, 1H).

Example 7. Synthesis of Compound MT-004B

Compound MT-004A (0.5 g, 2.3 mmol) was dissolved in a solution of mixture of HCl:H$_2$O:THF=1:6:7 (12 mL), the reaction was run at room temperature for 12 hours and monitored by TLC, after the reaction was complete, an aqueous solution of $K_2CO_3$ was added to adjust pH to neutral, extracted 3 times with ethyl acetate (15 mL×3), the organic layers were combined and dried over anhydrous $Na_2SO_4$ and then passed through with anhydrous HCl gas, white solid was precipitated, than the resulting mixture was allowed to stand for 1-2 hours, and filtered to give the compound MT-004B as a white solid (0.39 g, 82%). ESI-MS: $[M+H]^+$ m/z 174.1. $^1$H-NMR (DMSO-d6, 300 MHz) δ: 3.32 (s, 1H), 3.76 (t, J=2.4 Hz, 1H), 3.89 (d, J=10.5 Hz, 2H), 4.23 (d, J=34.2 Hz, 2H), 4.43 (s, 1H), 7.41 (m, 1H), 7.85 (m, 3H), 10.05 (s, 1H).

Example 8. Synthesis of Compound MT-005

Compound MT-004B (0.25 g, 1.2 mmol) was taken, and added with an aqueous solution of $NaHCO_3$ to be neutralized to neutral, extracted with ethyl acetate, spin-dried, and the resulting substance was dissolved in 25 mL of ethanol, and then t-butyl hydroxylamine (0.2 g, 2.4 mmol) was added, the reaction was run at room temperature for 8 hours and monitored by TLC, after the reaction was complete, the solvent was evaporated to dryness under reduced pressure, and the resulting material was separated with silica gel column chromatography (ethyl acetate:petroleum ether=1:1) to give the compound MT-005 as a colorless oil (0.19 g, 65%). ESI-MS: $[M+H]^+$ m/z 245.1. $^1$H-NMR (CDCl$_3$, 300 MHz) δ: 1.61 (s, 9H), 2.01 (s, 1H), 2.27 (t, J=2.4 Hz, 1H), 3.43 (d, J=2.4 Hz, 2H), 3.91 (s, 2H), 7.40 (m, 2H), 7.56 (s, 1H), 8.12 (m, 1H), 8.36 (s, 1H).

Example 9. Synthesis of Compound MT-004

Compound MT-005 (0.37 g, 1.5 mmol) was dissolved in methanol (30 mL), $NaHCO_3$ (0.13 g, 1.5 mmol) and $CH_3I$ (0.2 g, 1.5 mmol) were added respectively, the reaction was run for 1 hour at room temperature and monitored by TLC. After the reaction was complete, the solvent was evaporated, water was added, extracted three times with ethyl acetate (20 mL×3), the organic layers were combined and dried over anhydrous $Na_2SO_4$, the solvent was evaporated under reduced pressure, the resulting material was separated with silica gel column chromatography (ethyl acetate:petroleum ether=1:2) to give the compound MT-004A as a pale yellow oil (0.23 g, 60%). ESI-MS: $[M+H]^+$ m/z 259.0. $^1$H-NMR (DMSO-d6, 300 MHz) δ: 1.50 (s, 9H), 2.20 (s, 3H), 3.19 (t, J=2.4 Hz, 1H), 3.28 (d, J=2.4 Hz, 2H), 3.51 (s, 2H), 7.35 (m, 2H), 7.84 (s, 1H), 8.23 (d, J=7.5 Hz, 1H), 8.33 (s, 1H).

Example 10. Synthesis of Compound MT-006

Compound MT-005 (0.37 g, 1.5 mmol) was dissolved in methanol (30 mL), $NaHCO_3$ (0.13 g, 1.5 mmol) and propargyl bromide (0.18 g, 1.5 mmol) were added respectively, the reaction was refluxed for 2 hours and monitored by TLC. After the reaction was complete, the solvent was evaporated, water was added and extracted three times with ethyl acetate (20 mL×3), the organic layers were combined and dried over anhydrous $Na_2SO_4$, the solvent was evaporated under reduced pressure, and the resulting material was separated with silica gel column chromatography (ethyl acetate:petroleum ether=1:3) to give the compound MT-006 as a white solid (0.28 g, 68%). ESI-MS: $[M+H]^+$ m/z 283.0. $^1$H-NMR (DMSO-d6, 300 MHz) δ: 1.50 (s, 9H), 3.22 (t, J=2.4 Hz, 2H), 3.33 (d, J=2.4 Hz, 4H), 3.62 (s, 2H), 7.35 (m, 2H), 7.85 (s, 1H), 8.25 (d, J=7.5 Hz, 1H), 8.33 (s, 1H).

Example 11. Synthesis of Compound MT-007A m-Hydroxybenzaldehyde (1.22 g, 10 mmol) was dissolved in ethanol (50 mL), t-butyl hydroxylamine (1.78 g, 20 mmol) was added, and the reaction was refluxed for 6 hours at 75° C. and monitored by TLC. After the reaction was complete, the solvent was evaporated to dryness under reduced pressure, and the resulting material was separated with silica gel column chromatography (ethyl acetate:petroleum ether=1:1) to give the compound MT-007A as a white solid (1.35 g, 70%). ESI-MS: $[M+H]^+$ m/z 194.0. $^1$H-NMR (DMSO-d6, 300 MHz) δ: 1.49 (s, 9H), 6.81 (s, 1H), 7.20 (t, J=7.8 Hz, 1H), 7.55 (d, J=7.8 Hz, 1H), 7.72 (s, 1H), 8.07 (d, J=0.9 Hz, 1H), 9.47 (s, 1H).

Example 12. Synthesis of Compound MT-007

Compound MT-007A (0.25 g, 1.3 mmol) was dissolved in 20 mL of dry $CH_2Cl_2$, then NaOH (0.1 g, 2.6 mmol) was added at room temperature, stirred for 1 hour, and N-methyl-ethyl-N-carbamoyl chloride (0.31 g, 2.6 mmol) was added, the reaction was run for 3 hours and monitored by TLC. After the reaction was complete, 15 mL of water was added, extracted three times with $CH_2Cl_2$ (20 mL×3), the organic layers were combined and dried over anhydrous $Na_2SO_4$, the solvent was evaporated under reduced pressure, and the resulting material was separated with silica gel column chromatography (ethyl acetate:petroleum ether=1:2) to give the compound MT-007 as a white solid (0.24 g, 67%). ESI-MS: $[M+H]^+$ m/z 278.8. $^1$H-NMR (DMSO-d6, 300 MHz) δ: 1.15 (m, 3H), 1.50 (s, 9H), 2.97 (d, J=37.8 Hz, 3H), 3.32 (m, 2H), 7.15 (m, 1H), 7.42 (t, J=7.8 Hz, 1H), 7.90 (s, 1H), 8.00 (d, J=7.8 Hz, 1H), 8.35 (s, 1H).

Example 13. Synthesis of Compound MT-008A p-Hydroxybenzaldehyde (0.61 g, 5 mmol) was dissolved in ethanol (50 mL), then t-butyl hydroxylamine (0.89 g, 10 mmol) was added, the reaction was refluxed for 6 hours at 75° C. and monitored by TLC. After the reaction was complete, the solvent was evaporated under reduced pressure, and the resulting material was separated with silica gel column chromatography (ethyl acetate:petroleum ether=1:1) to give the compound MT-008A as a white solid (0.73 g, 76%). ESI-MS: $[M+H]^+$ m/z 194.1. $^1$H-NMR (CDCl$_3$, 300 MHz) δ: 1.64 (s, 9H), 7.67 (s, 1H), 7.93 (d, J=8.7 Hz, 2H), 8.44 (d, J=8.7 Hz, 2H), 10.03 (s, 1H).

Example 14. Synthesis of Compound MT-008

Compound MT-008A (0.25 g, 1.3 mmol) was dissolved in 20 mL of dried $CH_2Cl_2$, NaOH (0.1 g, 2.6 mmol) was added at room temperature, stirred for 1 hour, N-methyl-ethyl-N-carbamoyl chloride (0.31 g, 2.6 mmol) was added, and the reaction was run for 3 hours and monitored by TLC. After the reaction was complete, 15 mL of water was added, extracted three times with $CH_2Cl_2$ (20 mL×3), the organic layers were combined and dried over anhydrous $Na_2SO_4$, the solvent was evaporated under reduced pressure, and the resulting material was separated with silica gel column chromatography (ethyl acetate:petroleum ether=1:2) to give the compound MT-008 as a white solid (0.22 g, 60%). ESI-MS: $[M+H]^+$ m/z 279.0. $^1$H-NMR (DMSO-d6, 300

MHz) δ: 1.14 (m, 3H), 1.50 (s, 9H), 2.96 (d, J=36.3 Hz, 3H), 3.35 (m, 2H), 7.16 (d, J=8.7 Hz, 2H), 7.85 (s, 1H), 8.39 (d, J=8.7 Hz, 2H).

Example 15. Synthesis of Compound MT-009A

TMP (6.8 g, 50 mmol) was dissolved in dioxane (100 mL), selenium dioxide (11.1 g, 100 mmol) was added, and the reaction was heated to 107° C. for 3 hours and monitored by TLC. After the reaction was complete, the reaction mixture was filtered with cooling, the filtrate was distilled off the solvent and added with an appropriate amount of 100-200 mesh silica gel, and the sample was loaded and separated on a silica gel column ($CH_2Cl_2$ as eluent) to give the compound MT-009A as a pale yellow solid (2.46 g, 30%).

Example 16. Synthesis of Compound MT-009B

Compound MT-009A (2.46 g, 15 mmol) was dissolved in 30 mL of 1,2-dichloroethane, stirred until dissolved, triacetoxy sodium borohydride (1.59 g, 7.5 mmol) was added portionwise, and the reaction was run at room temperature for 7 hours. After the reaction was complete, the reaction mixture was filtered, pH of the filtrate was adjusted to neutral, 30 mL of water was added, and extracted three times with ethyl acetate (25 mL×3), the organic layers were combined and dried over anhydrous $Na_2SO_4$, the solvent was evaporated under reduced pressure, and the resulting material was separated with silica gel column chromatography (ethyl acetate:petroleum ether=1:2) to give the compound MT-009B as a white solid (1.2 g, 48%). ESI-MS: [M+H]$^+$ m/z 167.0. $^1$H-NMR (DMSO-d6): 10.09 (s, 1H); 5.41 (t, 1H); 4.68 (d, 2H); 2.73 (s, 3H); 2.61 (s, 3H).

Example 17. Synthesis of Compound MT-009C

Compound MT-009B (1.2 g, 7.2 mmol) was dissolved in 20 mL of 1,2-dichloroethane, stirred to dissolution, propargylamine (0.6 g, 10.8 mmol) was added, the reaction was run for 3 hours, then sodium triacetoxyborohydride (2.28 g, 10.8 mmol) was added, the reaction was run at room temperature for 3 hours and monitored by TLC. After the reaction was complete, an aqueous solution of $NaHCO_3$ was added to adjust pH to neutral, and then extracted three times with methylene chloride (20 mL×3), the organic layers were combined and dried over anhydrous $Na_2SO_4$, the solvent was evaporated under reduced pressure, and the resulting material was separated with silica gel column chromatography (ethyl acetate:petroleum ether=3:1) to give the compound MT-009C as a yellow solid (0.98 g, 67%). ESI-MS: [M+H]$^+$ m/z 205.8. $^1$H-NMR (CDCl$_3$, 300 MHz) δ: 2.22 (t, J=2.4 Hz, 1H), 2.37 (s, 3H), 2.48 (s, 3H), 3.49 (dd, J=0.6 Hz, 2.4 Hz, 2H), 3.91 (s, 2H), 4.61 (s, 2H).

Example 18. Synthesis of Compound MT-009D

Compound MT-009C (0.8 g, 3.9 mmol) was dissolved in 25 mL of THF, $NaHCO_3$ (0.66 g, 7.8 mmol) and di-tert-butyl dicarbonate (1.7 g, 7.8 mmol) were added respectively, the reaction was run at room temperature for 20 hours and monitored by TLC. After the reaction was complete, the solvent was evaporated to dryness, 30 mL of water were added, the organic layers were combined and dried over anhydrous $Na_2SO_4$, the solvent was evaporated under reduced pressure, and the resulting material was separated with silica gel column chromatography (ethyl acetate:petroleum ether=1:3) to give the compound MT-009D as a colorless oil (0.94 g, 86%). ESI-MS: [M+H]$^+$ m/z 306.0. $^1$H-NMR (CDCl$_3$, 300 MHz) δ: 1.45 (m, J=25.2 Hz, 9H), 2.16 (s, 1H), 2.40 (s, 3H), 2.56 (s, 3H), 4.14 (d, J=35.7 Hz, 2H), 4.28 (s, 1H), 4.68 (s, 4H).

Example 19. Synthesis of Compound MT-009E

Compound MT-009D (0.9 g, 3 mmol) was dissolved in 25 mL of dry $CH_2Cl_2$, a powder of 60% NaH (0.24 g, 6 mmol) was added with ice-cooling, stirred for 1 hour, then N-ethyl-N-methyl carbamoyl chloride (0.73 g, 6 mmol) was added, the reaction was run with ice bath for 2 hours and then at room temperature for 4 hours and monitored by TLC. After the reaction was complete, 20 mL of water was added for quenching, and extracted 3 times with $CH_2Cl_2$ (20 mL×3), the organic layers were combined and dried over anhydrous $Na_2SO_4$, the solvent was evaporated under reduced pressure, and the resulting material was separated with silica gel column chromatography (ethyl acetate:petroleum ether=1:3) to give the compound MT-009E as a colorless oil (0.7 g, 60%). ESI-MS: [M+H]$^+$ m/z 391.2. $^1$H-NMR (CDCl$_3$, 300 MHz) δ: 1.12 (m, 3H), 1.45 (m, 9H), 2.16 (s, 1H), 2.52 (s, 6H), 2.89 (d, J=2.4 Hz, 3H), 3.30 (s, 2H), 4.16 (d, J=35.4 Hz, 2H), 4.65 (s, 2H), 5.20 (s, 2H).

Example 20. Synthesis of Compound MT-010

Compound MT-009E (0.5 g, 1.3 mmol) was dissolved in 20 of mL $CH_2Cl_2$, a solution of mixture of trifluoroacetic acid and $CH_2Cl_2$ (6 mL, volume ratio 1:4) was added dropwise with dropping funnel, and the reaction was run at room temperature for 30 min and monitored by TLC. After the reaction was complete, an aqueous solution of $NaHCO_3$ was added to adjust pH to neutral, extracted three times with $CH_2Cl_2$ (20 mL×3), the organic layers were combined and dried over anhydrous $Na_2SO_4$, the solvent was evaporated under reduced pressure, and the resulting material was separated with silica gel column chromatography (ethyl acetate:petroleum ether=1:3) to give the compound MT-010 as a colorless oil (0.17 g, 45%). ESI-MS: [M+H]$^+$ m/z 291.4. $^1$H-NMR (CDCl$_3$, 300 MHz) δ: 1.11 (d, J=5.1 Hz, 3H), 2.11 (s, 1H), 2.26 (t, J=2.4 Hz, 1H), 2.54 (s, 3H), 2.57 (s, 3H), 2.90 (d, J=10.5 Hz, 3H), 3.33 (m, 2H), 3.58 (d, J=2.4 Hz, 2H), 3.99 (s, 2H), 5.22 (s, 2H).

Example 21. Synthesis of Compound MT-009

Compound MT-010 (0.58 g, 2 mmol) was dissolved in 25 mL of methanol, $NaHCO_3$ (0.25 g, 3 mmol) and $CH_3I$ (0.43 g, 3 mmol) were added respectively, and the reaction was run at room temperature for 3 hours and monitored by TLC. After the reaction was complete, the solvent was evaporated, an aqueous solution of $NaHCO_3$ was added to adjust pH to neutral, extracted three times with ethyl acetate (25 mL×3), the organic layers were combined and dried over anhydrous $Na_2SO_4$, the solvent was evaporated under reduced pressure, and the resulting material was separated with silica gel column chromatography (ethyl acetate:petroleum ether=1:3) to give the compound MT-009 as a pale yellow oil (0.4 g, 65%). ESI-MS: [M+H]$^+$ m/z 305.1. $^1$H-NMR (CDCl$_3$, 300 MHz) δ: 1.06 (m, 3H), 2.24 (t, J=2.4 Hz, 1H), 2.29 (s, 3H), 2.51 (s, 3H), 2.53 (s, 3H), 2.84 (s, 3H), 3.26 (s, 2H), 3.34 (s, 2H), 3.65 (s, 2H), 5.15 (s, 2H).

Example 22. Synthesis of Compound MT-011

Compound MT-010 (0.58 g, 2 mmol) was dissolved in methanol (25 mL), then $NaHCO_3$ (0.25 g, 3 mmol) and propargyl bromide (0.35 g, 3 mmol) were added respectively, the reaction was run at room temperature for 3 hours and monitored by TLC. After the reaction ended, the solvent was evaporated, an aqueous solution NaHCO$_3$ was added to adjust pH to neutral, extracted three times with ethyl acetate (25 mL×3), the organic layers were combined and dried over anhydrous Na$_2$SO$_4$, the solvent was evaporated under reduced pressure, and the resulting material was separated with silica gel column chromatography (ethyl acetate:petroleum ether=1:3) to give the compound MT-011 as a pale yellow oil (0.5 g, 70%). ESI-MS: [M+H]$^+$ m/z 329.1. $^1$H-NMR (CDCl$_3$, 300 MHz) δ: 1.11 (d, J=5.1 Hz, 6.9 Hz, 3H), 2.27 (t, J=2.4 Hz, 2H), 2.55 (s, 3H), 2.61 (s, 3H), 2.89 (s, 3H), 3.47 (d, J=2.4 Hz, 4H), 3.83 (s, 2H), 5.21 (s, 2H).

Example 23. Synthesis of Compound TMP-OH

In a 500 ml round-bottom flask, TMP (13.6 g, 100 mmol) was added and dissolved in glacial acetic acid (15 mL), 30% hydrogen peroxide (8 mL, 75 mmol) was added, and reacted for 4 hours at 70° C., and 30% hydrogen peroxide (8 mL, 75 mmol) was added and then further reacted for 4 hours and monitored by TLC until the reaction product was no longer generated. The resulting material was allowed to return to room temperature then placed in an ice bath, adjusted to pH 10 with a solution of 10% sodium hydroxide, extracted with chloroform, dried over anhydrous sodium sulfate, and filtered and concentrated to give crude material of TMP nitric oxide. Without isolation, the crude material was added with acetic anhydride (14.3 mL, 150 mmol), heated to 125° C. with reflux for 3 hours, and monitored by TLC until the starting material completely consumed, and the excess acetic anhydride was removed by distillation to give TMP acetyl compound, allowed to return to room temperature then placed in an ice bath, a solution of 10% sodium hydroxide was added to adjust pH to 12, stirred for 5 hours at room temperature, extracted with chloroform, dried over anhydrous sodium sulfate, filtered and concentrated, and the resulting material as separated with column chromatography eluted with ethyl acetate/petroleum ether (1:1) to give the compound TMP-OH as a white solid (9.88 g, 65%).

Example 24. Synthesis of Compound TMP-CHO

In a 50 ml round-bottom flask, the compound TMP-OH (1.52 g, 10 mmol) was added and dissolved in 20 mL of anhydrous ethanol, active manganese dioxide (2.61 g, 30 mmol) was added, heated to reflux for 3 hours, and monitored by TLC until the starting material completely consumed, and the resulting material was filtered and concentrated, and separated with column chromatography eluted with ethyl acetate/petroleum ether (1:1) to give the compound TMP-CHO as a white solid (0.99 g, 66%).

Example 25. Synthesis of Compound TMP-012

In a 50 mL round-bottom flask, freshly prepared TMP-CHO (150 mg, 1 mmol) was added and dissolved in 20 mL of 1,2-dichloroethane, propargylamine (66 mg, 1.2 mmol) was added slowly at room temperature, the reaction was run at room temperature for 2 hours, triacetoxy sodium borohydride (424 mg, 2 mmol) was added and monitored by TLC, about 2 hours later the reaction was complete, 10 mL of 10% K$_2$CO$_3$ was added for quenching. The resulting material was extracted with dichloromethane, dried over anhydrous sodium sulfate, filtered and concentrated, and purified with silica gel column chromatography (ethyl acetate:petroleum ether 3:2) to give the compound MT-012 as a yellow solid (163 mg, 86%). ESI-MS: [M+H]$^+$ m/z 190.3. $^1$H-NMR (CDCl$_3$): 3.96 (s, 2H); 3.56 (d, J=2.4 Hz, 2H); 2.51 (s, 3H); 2.49 (s, 6H); 2.26 (t, J=2.4 Hz, 1H).

Example 26. Synthesis of Compound TMP-013

In a 50 mL round-bottom flask, the compound MT-012 (189 mg, 1 mmol) was added and dissolved in 15 mL of acetone, anhydrous potassium carbonate (276 mg, 2 mmol) and iodomethane (170 μL, 1.2 mmol) were added, stirred for at room temperature 5 min, then heated to reflux for 3 hours, and monitored by TLC until the starting material disappeared completely. The resulting material was filtered and concentrated, and purified with silica gel column chromatography (ethyl acetate:petroleum ether 1:3) to give the compound MT-013 as a white solid (179 mg, 88%). ESI-MS: [M+H]+ m/z 204.4 1H-NMR (CDCl3): 3.70 (s, 2H); 3.40 (d, J=2.4 Hz, 2H); 2.58 (s, 3H); 2.51 (s, 3H); 2.50 (s, 3H); 2.35 (s, 3H); 2.29 (t, J=2.4 Hz, 1H).

Example 27. Synthesis of Compound TMP-014

In a 50 mL round-bottom flask, the compound MT-012 (189 mg, 1 mmol) was added and dissolved in methanol (15 mL), anhydrous potassium carbonate (276 mg, 2 mmol) and propargyl bromide (177 mg, 1.5 mmol) were added, stirred at room temperature for 5 min and then heated to reflux for 3 hours, and monitored by TLC until the starting material disappeared completely. The resulting material was filtered and concentrated, purified with silica gel column chromatography (ethyl acetate:petroleum ether 1:3) to give the compound MT-014 as a white solid (186 mg, 82%). ESI-MS: [M+H]+ m/z 228.3 1H-NMR (CDCl3): 3.82 (s, 2H); 3.47 (d, J=2.4 Hz, 4H); 2.60 (s, 3H); 2.50 (s, 6H); 2.27 (t, J=2.4 Hz, 2H).

Example 28. Synthesis of Compound TMP-015A

In a 500 mL round-bottom flask, the compound MT-009A (3.28 g, 200 mmol) was added and dissolved in 20 mL of toluene, p-toluenesulfonic acid (catalytic amount) and ethylene glycol (556 μL, 100 mmol) were added, the reaction was heated to 80° C. and monitored by TLC, after about 2.5 hours the reaction was complete, and the resulting material was filtered, concentrated and purified with silica gel column chromatography (ethyl acetate:petroleum ether 1:6) to give the compound MT-015A as a white solid (187 mg, 90%). ESI-MS: [M+H]$^+$ m/z 209.6. $^1$H-NMR (CDCl$_3$): 10.19 (s, 1H); 6.01 (s, 1H); 4.27 (m, 2H); 4.13 (m, 2H); 2.85 (s, 3H); 2.72 (s, 3H).

Example 29. Synthesis of Compound MT-015B

In a 50 mL round-bottom flask, the compound MT-015A (208 mg, 1 mmol) was added and dissolved in 20 mL of 1,2-dichloroethane, then propargylamine (66 mg, 1.2 mmol) was slowly added at room temperature, reacted at room temperature for 2 hours, sodium triacetoxyborohydride (424 mg, 2 mmol) was added, the reaction as monitored by TLC, and about 2 hours later the reaction was complete, then 10 mL of 10% K$_2$CO$_3$ was added for quenching, and the resulting material was extracted with dichloromethane, dried over anhydrous sodium sulfate, filtered and concentrated, and purified with silica gel column chromatography (ethyl acetate:petroleum ether 4:1) to give the compound of MT-015B as a yellow solid (203 mg, 82%). ESI-MS:

[M+H]$^+$ m/z 248.1. $^1$H-NMR (CDCl$_3$): 5.95 (s, 1H); 4.25 (m, 2H); 4.09 (m, 2H); 4.00 (s, 2H); 3.57 (d, 2H); 2.62 (s, 3H); 2.56 (s, 3H); 2.25 (t, 1H)

Example 30. Synthesis of Compound MT-015C

In a 50 mL round-bottom flask, the compound MT-015B (247 mg, 1 mmol) was added and dissolved in 15 mL of acetone, then anhydrous potassium carbonate (276 mg, 2 mmol) and iodomethane (170 μl, 1.2 mmol) were added, and the reaction was stirred for 5 minutes, heated to reflux for 3 hours and monitored by TLC until the starting material disappeared completely, and the resulting material was filtered and the filtrate was concentrated and purified with silica gel column chromatography (ethyl acetate:petroleum ether 1:2) to give a white solid MT-015C (201 mg, 80%). ESI-MS: [M+H]$^+$ m/z 262.1. $^1$H-NMR (CDCl$_3$): 5.95 (s, 1H); 4.26 (m, 2H); 4.09 (m, 2H); 3.73 (s, 2H); 3.40 (d, 2H); 2.62 (s, 6H); 2.34 (s, 3H); 2.28 (t, 1H).

Example 31. Synthesis of Compound MT-015D

In a 50 mL round-bottom flask, the compound MT-015C (261 mg, 1 mmol) was added, then a 10 mL solution of mixture of 37% HCl/H$_2$O/THF (1:6:7) was added, stirred at room temperature for 5 hours, an aqueous solution of 10% K$_2$CO$_3$ was added to adjust pH to 10, extracted with dichloromethane, dried over anhydrous sodium sulfate, filtered and concentrated, and the resulting material was purified with silica gel column chromatography (ethyl acetate:petroleum ether 1:3) to give the compound MT-015D as a white solid (200 mg, 92%). ESI-MS: [M+H]$^+$ m/z 218.4. $^1$H-NMR (CDCl$_3$): 10.18 (s, 1H); 3.80 (s, 2H); 3.43 (d, 2H); 2.84 (s, 3H); 2.70 (s, 3H); 2.37 (s, 3H); 2.31 (t, 1H).

Example 32. Synthesis of Compound MT-015

In a 50 mL round-bottom flask, the compound MT-015D (217 mg, 1 mmol) was added and dissolved in 10 mL of anhydrous ethanol, a 10 mL solution of tert-butyl hydroxylamine (178 mg, 2 mmol) in ethanol was added dropwise under N$_2$ protection. The reaction was run at room temperature and monitored by TLC for about 5 hours until the starting material disappeared, and the resulting material was concentrated and purified with silica gel column chromatography (ethyl acetate:petroleum ether 2:1) to give the compound MT-015 as a white solid (173 mg, 60%). ESI-MS: [M+H]+ m/z 289.2. 1H-NMR (CDCl3): 7.84 (s, 1H); 3.75 (s, 2H); 3.41 (d, 2H); 2.62 (s, 3H); 2.51 (s, 3H); 2.35 (s, 3H); 2.29 (t, 1H); 1.65 (s, 9H).

Example 33. Synthesis of Compound MT-016A

In a 50 mL round-bottom flask, the compound MT-015B (247 mg, 1 mmol) was added and dissolved in methanol (15 mL), anhydrous potassium carbonate (276 mg, 2 mmol) and propargyl bromide (177 mg, 1.5 mmol) were added, the reaction was stirred at room temperature for 5 minutes, and heated to reflux for 3 hours and monitored by TLC until the starting material disappeared, and the resulting material was filtered and the filtrate was concentrated and purified with silica gel column chromatography (ethyl acetate:petroleum ether 1:3) to give the compound MT-016A as a white solid (205 mg 72%). ESI-MS: [M+H]$^+$ m/z 286.2. $^1$H-NMR (CDCl$_3$): 5.96 (s, 1H); 4.27 (m, 2H); 4.10 (m, 2H); 3.86 (s, 2H); 3.48 (d, 4H); 2.65 (s, 3H); 2.63 (s, 3H); 2.28 (t, 2H).

Example 34. Synthesis of Compound MT-016B

In a 50 mL round-bottom flask, the compound MT-016A (281 mg, 1 mmol) was added, a 10 mL solution of mixture of 37% HCl/H$_2$O/THF (1:6:7) was added, stirred at room temperature for 5 minutes, an aqueous solution of 10% K$_2$CO$_3$ was added to adjust pH=10, extracted with dichloromethane, dried over anhydrous sodium sulfate, filtered and concentrated after, and the resulting material was purified with silica gel column chromatography (ethyl acetate:petroleum ether 1:3) to give the compound MT-016B as a white solid (202 mg, 84%). ESI-MS: [M+H]$^+$ m/z 242.3. $^1$H-NMR (CDCl$_3$): 10.20 (s, 1H); 3.94 (s, 2H); 3.51 (d, 4H); 2.85 (s, 3H); 2.74 (s, 3H); 2.30 (t, 2H).

Example 35. Synthesis of Compound MT-016

In a 50 mL round-bottom flask, the compound MT-016B (241 mg, 1 mmol) was added and dissolved in 10 mL of anhydrous ethanol, a 10 mL ethanol solution of tert-butylhydroxylamine (178 mg, 2 mmol) was added dropwise under N$_2$ protection, and the reaction was run at room temperature and monitored by TLC, about 5 hours later the starting material disappeared completely, and the resulting material was concentrated and purified with silica gel column chromatography (ethyl acetate:petroleum ether 2:1) to give the compound MT-016 as a white solid (222 mg 71%). ESI-MS: [M+H]$^+$ m/z 313.2. $^1$H-NMR (CDCl$_3$): 7.84 (s, 1H); 3.87 (s, 2H); 3.49 (d, 4H); 2.64 (s, 3H); 2.51 (s, 3H); 2.28 (t, 2H); 1.65 (s, 9H).

Example 36. Synthesis of Compound MT-017

In a 50 mL round-bottom flask, the compound TMP-OH (152 mg, 1 mmol) was added and dissolved in 20 mL of anhydrous dichloromethane, and NaH (48 mg, 2 mmol) (60% substance-in-oil) and N-methyl-N-ethylcarbamoyl chloride (242 mg, 2 mmol) were added, the resulting turbid solution was reacted at room temperature under N$_2$ protection and monitored by TLC, 5 hours later when no product was further generated, 10 mL of H$_2$O was added carefully for quenching, the resulting material was extracted with dichloromethane, dried over anhydrous sodium sulfate, filtered and concentrated, and purified with silica gel column chromatography (ethyl acetate:petroleum ether 1:3) to give the product of MT-017 as a yellow oil (142 mg 60%). ESI-MS: [M+H]$^+$ m/z 238.2. $^1$H-NMR (CDCl$_3$): 5.21 (s, 2H); 3.32 (m, 2H); 2.90 (d, 3H); 2.55 (s, 3H); 2.51 (s, 6H); 1.11 (m, 3H).

Example 37. Synthesis of Compound MT-018A

In a 50 mL round-bottom flask, the compound MT-009B (166 mg, 1 mmol) was added and dissolved in 10 mL of anhydrous ethanol, a 10 mL solution of tert-butyl-hydroxylamine (178 mg, 2 mmol) in ethanol was added dropwise under N$_2$ protection, the reaction was run at room temperature and monitored with TLC for 7 hours until the starting material disappeared completely, and the resulting material was concentrated and purified with silica gel column chromatography (ethyl acetate:petroleum ether 4:1) to give the compound MT-018A as a white solid (123 mg, 52%). ESI-MS: [M+H]$^+$ m/z 238.3. $^1$H-NMR (CDCl$_3$): 7.87 (s, 1H); 4.74 (s, 2H); 2.53 (s, 3H); 2.45 (s, 3H); 1.65 (s, 9H).

Example 38. Synthesis of Compound MT-018B

In a 50 mL round-bottom flask, the compound MT-018A (237 mg, 1 mmol) was added and dissolved in 20 mL of anhydrous dichloromethane, and NaH (48 mg, 2 mmol) (60% substance-in-oil) and N-methyl-N-ethylcarbamoyl chloride (242 mg, 2 mmol) were added, resulting turbid solution was reacted at room temperature under $N_2$ protection and monitored by TLC, 5 hours later when no product was further generated, 10 mL of $H_2O$ was added carefully for quenching, the resulting material was extracted with dichloromethane, dried over anhydrous sodium sulfate, filtered and concentrated, and purified with silica gel column chromatography (ethyl acetate:petroleum ether 2:1) to give the compound MT-018 as a white solid (274 mg 85%). ESI-MS: [M+H]$^+$ m/z 323.3. $^1$H-NMR (CDCl$_3$): 7.86 (s, 1H); 5.25 (s, 2H); 3.31 (m, 2H); 2.91 (d, 3H); 2.59 (s, 3H); 2.51 (s, 3H); 1.65 (s, 9H); 1.12 (m, 3H).

Example 39. Synthesis of Compound MT-019A

3-Hydroxyacetophenone (20 g, 147 mmol) was dissolved in 250 mL of methanol, and propargylamine (12 mL, 176 mmol) was added with stirring, concentrated hydrochloric acid was added dropwise to adjust pH to neutral, sodium cyanoborohydride (18.5 g, 294 mmol) was added, and the reaction was run at reflux and monitored by TLC, 8 hours later when the reaction was complete. Methanol was evaporated to dryness under reduced pressure, 100 mL of water and 300 mL of ethyl acetate were added for extraction, the organic layer was taken and extracted with 5% hydrochloric acid, and the acidic water layer was taken, and added with a solution of 10% sodium hydroxide to adjust pH to 7-8, allowed to stand to have solid precipitated, filtered, and the filter residue was washed 3 times with ice water (50 mL×3) to give 12 g of the compound MT-019A. The filtrate was extracted with ethyl acetate 3 times (100 mL×3), the combined organic layers were dried over anhydrous Na2SO$_4$, the solvent was evaporated to dryness under reduced pressure, and the resulting material was purified with silica gel column chromatography (ethyl acetate:petroleum ether 1:3) to give 10 g of the compound MT-019A. Overall yield: 85%. ESI-MS: [M+H]$^+$ m/z 176.0. $^1$H-NMR: (300 MHz, DMSO-d6) δ: 9.27 (s, 1H), 7.08 (t, J=8.0 Hz, 1H), 6.71 (m, 2H), 6.60 (m, 2H), 3.78 (q, J=6.5 Hz, 1H), 3.21 (dd, J=16.9, 2.4 Hz, 1H), 3.02 (t, J=2.4 Hz, 1H), 2.96 (dd, J=16.9, 2.4 Hz, 1H), 2.34 (s, 1H), 1.19 (d, J=6.6 Hz, 3H).

Example 40. Synthesis of Compound MT-019B

Compound MT-019A (18 g, 103 mmol) was dissolved in 250 mL of THF, and triethylamine (43 mL, 308 mmol) and di-tert-butyl dicarbonate ester (33 mL, 154 mmol) were added with stirring at room temperature, and the reaction was run at room temperature and monitored by TLC throughout the reaction, 26 hours later the reaction was complete, THF was evaporated under reduced pressure, 200 mL of water was added, extracted 2 times with 200 mL of ethyl acetate, the organic layers were combined and dried over anhydrous Na$_2$SO$_4$, the solvent was evaporated under reduced pressure, and the resulting material was purified by silica gel column chromatography (ethyl acetate:petroleum ether 1:6) to give 20 g of the compound MT-019B, yield: 71%. ESI-MS: [M+H]$^+$ m/z 276.4. $^1$H-NMR: (300 MHz, DMSO-d6) δ: 9.35 (s, 1H), 7.13 (t, J=7.8 Hz, 1H), 6.67 (m, 3H), 5.09 (s, 1H), 3.94 (d, J=18.9 Hz, 1H), 3.58 (d, J=18.9 Hz, 1H), 3.06 (t, J=2.3 Hz, 1H), 1.50 (d, J=7.1 Hz, 3H), 1.38 (s, 9H).

Example 41. Synthesis of Compound MT-019C

Compound MT-019B (11 g, 40 mmol) was dissolved in 200 mL of anhydrous acetonitrile, and paraformaldehyde (8.4 g, 280 mmol), anhydrous magnesium chloride (5.7 g, 60 mmol), and triethylamine (22.3 mL, 160 mmol) were added in sequence, the reaction was run at reflux and monitored by TLC, 1 hour later the reaction was complete and allowed to return to room temperature, 100 mL of water was added for quenching, 5% hydrochloric acid was used to adjust pH to neutral, extracted three times with ethyl acetate (150 mL×3), the organic layers were combined and dried over anhydrous Na$_2$SO$_4$, the solvent was evaporated to dryness under reduced pressure, and the resulting material was purified with silica gel column chromatography (ethyl acetate:petroleum ether 1:5) to give 12 g of the compound MT-019C, yield: 99%. ESI-MS: [M+H]$^+$ m/z 304.5. $^1$H-NMR: (300 MHz, CDCl$_3$) δ: 11.04 (s, 1H), 9.87 (s, 1H), 7.52 (d, J=8.0 Hz, 1H), 6.99 (m, 1H), 6.95 (s, 1H), 5.30 (s, 1H), 4.03 (s. 1H), 3.65 (s, 1H), 2.16 (s, 1H), 1.64 (d, J=7.1 Hz, 1H), 1.45 (s, 9H).

Example 42. Synthesis of Compound MT-019D

Compound MT-019C (8.0 g, 26 mmol) was dissolved in 200 mL of dichloromethane with 25% trifluoroacetic acid, the reaction was run at room temperature and monitored by TLC throughout the process, and, after 2 hours, the reaction was complete. Saturated NaHCO$_3$ solution was added to adjust pH to neutral, and the methylene chloride layer was separated, the aqueous layer was extracted three times with ethyl acetate (100×3), and the organic layers were combined and dried over anhydrous Na$_2$SO$_4$, the solvent was evaporated to dryness under reduced pressure, and the resulting material was purified with silica gel column chromatography (ethyl acetate:petroleum ether 1:3) to give 5.1 g of the compound MT-019D, yield: 95%. ESI-MS: [M+H]$^+$ m/z 204.0. $^1$H-NMR: (300 MHz, DMSO-d6) δ: 10.65 (s, 1H), 10.18 (s, 1H), 7.61 (d, J=8.0 Hz, 1H), 6.97 (d, J=1.1 Hz, 1H), 6.92 (dd, J=8.0, 1.1 Hz, 1H), 3.88 (q, J=6.5 Hz, 1H), 3.26 (dd, J=17.7, 1.9 Hz, 1H), 2.99 (dd, J=17.7, 2.4 Hz, 1H), 3.02 (t, J=2.4 Hz, 1H), 2.34 (s, 1H), 1.22 (d, J=6.6 Hz, 3H).

Example 43. Synthesis of Compound MT-019E

Nitro-t-butane (10.0 g, 97 mmol) was dissolved in 200 mL of anhydrous ethanol in an ice bath. (7.6 g, 116 mmol) active zinc was added, after the temperature dropped to below 5° C., glacial acetic acid (10 mL, 175 mmol) was added slowly dropwise, after the addition, the ice bath was removed, and the reaction was continued at room temperature for 3 hours. To the reaction solution was added the compound MT-019D (5 g, 24.6 mmol), the reaction was run at room temperature and monitored by TLC until 16 hours later when the reaction was complete. Most of the ethanol was distilled off under reduced pressure, 100 mL of water and 200 mL of ethyl acetate were added and stirred for 5 minutes, the resulting mixture was filtered and the organic layer was separated, the aqueous layer was extracted three times with ethyl acetate (100 mL×3), and the organic layers were combined and dried over anhydrous Na$_2$SO$_4$, the solvent was evaporated to dryness under reduced pressure, and the resulting material was purified with silica gel column chromatography (ethyl acetate:petroleum ether 1:2) to give 6.0 g of MT-019E, yield: 89%. ESI-MS: [M+H]$^+$ m/z 274.9. $^1$H-NMR: (300 MHz, DMSO-d6) δ: 12.72 (s, 1H), 8.07 (s, 1H), 7.44 (d, J=8.1 Hz, 1H), 6.82 (dd, J=8.0, 1.7 Hz, 1H), 6.76 (d, J=1.5 Hz, 1H), 3.83 (q, J=6.5 Hz, 1H), 3.23 (dd, J=16.9, 2.5 Hz, 1H), 3.03 (t, J=2.4 Hz, 1H), 2.97 (dd, J=16.9, 2.3 Hz, 1H), 2.48 (s, 1H), 1.54 (s, 1H), 1.21 (d, J=6.5 Hz, 3H).

Example 44. Synthesis of Compound MT-019

Compound MT-019E (2.0 g, 7.3 mmol) was dissolved in 50 mL of anhydrous dichloromethane, sodium hydride (321 mg, 60%, 8 mmol) was added, the reaction was run at room temperature until no gas generated. N-methyl-N-ethylcarbamoyl chloride (886 μL) was added dropwise, the reaction was continued at room temperature and monitored by TLC. After 5 hours, the reaction was complete, and 20 mL of water was added for quenching, and stirred for 5 minutes. The organic layer was separated, and the aqueous layer was extracted three times with ethyl acetate (10 mL×3), the organic layers were combined and dried over anhydrous $Na_2SO_4$, the solvent was evaporated to dryness under reduced pressure, and the resulting material was purified with silica gel column chromatography (ethyl acetate:petroleum ether 1:1) to give 2.3 g of the compound MT-019, yield: 88%. ESI-MS: $[M+H]^+$ m/z 360.4. $^1$H-NMR: (300 MHz, DMSO-d6) δ: 9.15 (m, 1H), 7.60 (s, 1H), 7.22 (d, J=8.3 Hz, 1H), 7.15 (d, J=3.9 Hz, 1H), 3.91 (q, J=6.5 Hz, 1H), 3.50 (q, J=6.9 Hz, 1H), 3.33 (q, J=6.9 Hz, 1H), 3.24 (dd, J=17.0, 2.6 Hz, 1H), 3.10 (s, 1.5H), 3.04 (t, J=2.4 Hz, 1H), 2.98 (dd, J=17.0, 2.6 Hz, 1H), 2.93 (s, 1.5H), 2.54 (s, 1H), 1.48 (s, 9H), 1.23 (m, 4.5H), 1.12 (d, J=7.1 Hz, 1.5H).

Example 45. Synthesis of Compound MT-020

Compound MT-019 (2.0 g, 5.6 mmol) was dissolved in 50 mL of acetone with an ice bath, sodium bicarbonate (514 mg, 6.1 mmol) was added, methyl iodide (346 μL) was added slowly dropwise. The reaction was run with an ice bath and monitored by TLC, and was complete 1 hour later. The solvent was evaporated to dryness under reduced pressure, 100 mL of water and 100 mL of ethyl acetate were added for extraction, the organic layer was separated, the aqueous layer was extracted three times with ethyl acetate (50 mL×3), and the organic layers were combined and dried over anhydrous Na2SO$_4$, the solvent was evaporated to dryness under reduced pressure, and the resulting material was purified with silica gel column chromatography (ethyl acetate:petroleum ether 1:2) to give 1.5 g of the compound MT-020, yield: 72%. ESI-MS: $[M+H]^+$ m/z 374.2. $^1$H-NMR: (300 MHz, DMSO-d6) δ: 9.15 (m, 1H), 7.61 (s, 1H), 7.22 (d, J=8.3 Hz, 1H), 7.14 (d, J=4.5 Hz, 1H), 3.53 (m, 2H), 3.42 (dd, J=17.0, 2.8 Hz, 1H), 3.32 (q, J=6.9 Hz, 1H), 3.19 (dd, J=17.0, 2.8 Hz, 1H), 3.15 (s, 1H), 3.10 (s, 1.5H), 2.93 (s, 1.5H), 2.16 (s, 3H), 1.49 (s, 9H), 1.26 (d, J=6.6 Hz, 3H), 1.23 (t, J=7.1 Hz, 1.5H), 1.12 (t, J=7.1 Hz, 1.5H).

Example 46. Synthesis of Compound MT-021

Compound MT-019 (1.0 g, 2.8 mmol) was added and dissolved in 20 mL of methanol, NaHCO$_3$ (351 mg, 4.2 mmol) and 3-bromo-propyne (327 μL, 4.2 mmol) were added with stirring, and the reaction was run at room temperature and monitored by TLC, and 10 hours later, the reaction was complete. The solvent was evaporated to dryness under reduced pressure, 50 mL of water and 50 mL of ethyl acetate were added for extraction, the organic layer was separated, the aqueous layer was extracted three times with ethyl acetate (20 mL×3), and the organic layers were combined and dried over anhydrous Na2SO$_4$. The solvent was evaporated to dryness under reduced pressure, and the resulting material was purified with silica gel column chromatography (ethyl acetate:petroleum ether 1:3) to give 1.1 g of the compound MT-021, yield: 99%. ESI-MS: $[M+H]^+$ m/z 398.2. $^1$H-NMR: (300 MHz, $CD_3COCD_3$) δ: 9.36 (dd, J=8.3, 3.8 Hz, 1H), 7.74 (s, 1H), 7.28 (dd, J=8.3, 1.4 Hz, 1H), 7.23 (d, J=2.4 Hz, 1H), 3.73 (q, J=6.6 Hz, 1H), 3.60 (q, J=7.0 Hz, 1H), 3.50 (d, J=2.3 Hz, 4H), 3.41 (q, J=7.1 Hz, 1H), 3.20 (s, 1.5H), 3.00 (s, 1.5H), 2.74 (t, J=2.3 Hz, 2H), 1.57 (s, 9H), 1.38 (d, J=6.6 Hz, 3H), 1.32 (t, J=7.1 Hz, 1.5H), 1.18 (t, J=7.1 Hz, 1.5H).

Example 47. Synthesis of Compound MT-022A

R-6-hydroxy-1-aminoindan (500 mg, 3.35 mmol) was dissolved in 50 mL of methanol, then NaHCO$_3$ (563 mg, 6.7 mmol) and propargyl bromide (525 μL) were added in sequence, the reaction was run at reflux and monitored by TLC, and 10 hours later the reaction was complete. The resulting mixture was filtered, and the filtrate was evaporated to dryness under reduced pressure and purified with silica gel column chromatography (ethyl acetate:petroleum ether 1:3) to give 510 mg of the compound MT-022A, yield: 68%. ESI-MS: [M+H]+ m/z 226.5. $^1$H-NMR: (300 MHz, CDCl$_3$) δ: 7.03 (d, J=8.1 Hz, 1H), 6.90 (d, J=2.2 Hz, 1H), 6.72 (dd, J=8.1, 2.3 Hz, 1H), 5.99 (s, 1H), 4.54 (t, J=6.9 Hz, 1H), 3.50 (d, J=2.2 Hz, 4H), 2.88 (m, 1H), 2.69 (m, 1H), 2.24 (t, J=2.4 Hz, 2H), 2.19 (m, 2H).

Example 48. Synthesis of Compound MT-022B

Compound MT-022A (350 mg, 1.55 mmol) was dissolved in 20 mL of anhydrous acetonitrile, and anhydrous MgCl$_2$ (230 mg, 2.42 mmol), dry Et$_3$N (0.86 mL, 6.17 mmol) and paraformaldehyde (330 mg, 10.99 mmol) were added in sequence at room temperature, the reaction was run at reflux and monitored by TLC, and 2 hours later the reaction was complete and allowed to return to room temperature, 10 mL of water was added, 10% hydrochloric acid was used to adjust pH to 6, and the resulting material was extracted three times with ethyl acetate (20 mL×3), the organic layers were combined and dried over anhydrous Na2SO$_4$, the solvent was evaporated to dryness under reduced pressure, and the resulting material was purified with silica gel column chromatography (ethyl acetate:petroleum ether 1:3) to give 385 mg of the compound MT-022B, yield: 98%. ESI-MS: [M+H]+ m/z 254.3. $^1$H-NMR: (300 MHz, CDCl$_3$) δ: 11.08 (s, 1H), 9.86 (s, 1H), 7.38 (s, 1H), 7.07 (s, 1H), 4.57 (t, J=7.7 Hz, 1H), 3.54 (dd, J=7.7, 2.4 Hz, 4H), 2.97 (m, 1H), 2.77 (m, 1H), 2.30 (m, 1H), 2.27 (t, J=2.4 Hz, 3H), 2.18 (m, 1H).

Example 49. Synthesis of Compound MT-022C

Nitro-t-butane (10.0 g, 97 mmol) was dissolved in 200 mL of anhydrous ethanol with an ice bath, and (7.6 g, 116 mmol) active zinc was added until the temperature dropped to below 5° C., glacial acetic acid (10 mL, 175 mmol) was added slowly dropwise, and after the addition was complete, the ice bath was removed. The reaction was continued at room temperature for 3 hours. The above reaction mixture was added to MT-022B (3 g, 11.84 mmol), and the reaction was run at room temperature and monitored by TLC, and after 10 hours, the reaction was complete. Most of the ethanol was distilled off under reduced pressure, 100 mL of water and 200 mL of ethyl acetate were added, stirred for 5 minutes. The resulting mixture was filtered, and the organic layer of the filtrate was separated, the aqueous layer was extracted three times with ethyl acetate (100 mL×3), and the organic layers were combined and dried over anhydrous Na2SO$_4$. The solvent was evaporated to dryness under reduced pressure, and the resulting material was purified with silica gel column chromatography (ethyl acetate:petroleum ether 1:3) to give 3.45 g of the compound MT-022C, yield: 90%. ESI-MS: [M+H]+ m/z 325.3. $^1$H-NMR: (300 MHz, CDCl$_3$) δ: 12.16 (s, 1H), 7.69 (s, 1H), 7.03 (s, 1H), 6.94 (s, 1H), 4.52 (t, J=7.1 Hz, 1H), 3.51 (dd, J=5.0, 2.4 Hz, 4H), 2.86 (m, 1H), 2.68 (m, 1H), 2.23 (t, J=2.4 Hz, 2H), 2.19 (m, 2H), 1.62 (s, 9H).

Example 50. Synthesis of Compound MT-022

Compound MT-022 (3.0 g, 9.25 mmol) was dissolved in 50 mL of dichloromethane, and sodium hydroxide (444 mg, 11.1 mmol) was added, N-Methyl-N-ethylcarbamoyl chloride (403 µL) was added dropwise, and the reaction was run at room temperature and monitored by TLC, 3 hours later, the reaction was complete, then 20 mL of water was added, and stirred for 5 minutes. The organic layer was separated, the aqueous layer was extracted three times with ethyl acetate (10 mL×3), and the organic layers were combined and dried over anhydrous Na$_2$SO$_4$. The solvent was evaporated to dryness under reduced pressure, and purified with silica gel column chromatography (ethyl acetate:petroleum ether 1:2) to give 3.7 g of the compound MT-022, yield: 98%. ESI-MS: [M+H]+ m/z 411.0. $^1$H-NMR: (300 MHz, DMSO-d$_6$) δ: 9.11 (d, J=5.1 Hz, 1H), 7.63 (s, 1H), 7.04 (d, J=6.1 Hz, 1H), 4.55 (t, J=7.0 Hz, 1H), 3.50 (m, 1H), 3.40 (s, 4H), 3.32 (m, 1H), 3.18 (t, J=2.2 Hz, 2H), 3.02 (d, J=52.5 Hz, 3H), 2.89 (m, 1H), 2.75 (m, 1H), 2.17 (m, 2H), 1.49 (s, 9H), 1.17 (dt, J=33.1, 7.0 Hz, 3H).

Example 51. Synthesis of Compound MT-023A

R-(−)-1-aminoindan hydrochloride (7.0 g, 41.26 mmol) was taken, and added with a solution of 10% aqueous sodium hydroxide (100 mL), extracted with 200 mL of methylene chloride, the organic layers were separated and dried over anhydrous Na2SO$_4$, and filtered to remove Na$_2$SO$_4$. Trifluoroacetic anhydride (6.4 mL, 45.39 mmol) was dissolved in 100 mL of dichloromethane, and then added dropwise to a solution of the above material in dichloromethane with an ice bath. The reaction was run with the ice bath and monitored by TLC, 3.5 hours later the reaction was complete, then 100 mL of water was added, 10% sodium hydroxide solution was used to adjust pH to 7-8. The organic layer was separated, the aqueous layer was extracted three times with ethyl acetate, (20 mL×3), and the organic layers were combined and dried over anhydrous Na$_2$SO$_4$. The solvent was evaporated to dryness under reduced pressure and purified with silica gel column chromatography (ethyl acetate:petroleum ether 1:6) to give 7.8 g of the compound MT-023A, yield: 82%. ESI-MS: [M−H]+ m/z 228.07. $^1$H-NMR: (300 MHz, DMSO-d6) δ: 9.81 (d, J=7.7 Hz, 1H), 7.23 (m, 4H), 5.38 (q, J=7.8 Hz, 1H), 3.00 (m, 1H), 2.84 (m, 1H), 2.43 (m, 1H), 1.97 (m, 1H).

Example 52. Synthesis of Compound MT-023B

Anhydrous aluminum chloride (7.0 g, 52.36 mmol) was dissolved in anhydrous 1,2-dichloroethane (150 mL) with an ice bath, ethyl oxalyl chloride ester (5.9 mL, 52.36 mmol) was added dropwise, reacted for 30 minutes and the ice bath was removed, and compound MT-023A (4.0 g, 17.45 mmol) was added. The reaction was run at room temperature and monitored by TLC for 10 hours, then the reaction mixture was poured into crushed ice and stirred for 1 hour, the organic layer was separated, the aqueous layer was extracted twice with dichloromethane (50 mL×2), the organic layers were combined and dried over anhydrous Na$_2$SO$_4$. The solvent was evaporated to dryness under reduced pressure, and purified with silica gel column chromatography (ethyl acetate:petroleum ether 1:3) to give 5.4 g of the compound MT-023B, yield: 94%. ESI-MS: [M−H]$^+$ m/z 328.07. $^1$H-NMR: (300 MHz, DMSO-d6) δ: 9.91 (d, J=7.9 Hz, 1H), 7.88 (dd, J=7.9, 1.4 Hz, 1H), 7.73 (s, 1H), 7.54 (d, J=7.9 Hz, 1H), 5.44 (q, J=7.8 Hz, 1H), 4.42 (m, 2H), 3.10 (m, 1H), 2.96 (m, 1H), 2.51 (m, 1H), 2.06 (m, 1H), 1.33 (t, J=7.1 Hz, 2H).

Example 53. Synthesis of Compound MT-023C

Compound MT-023B (2.5 g, 7.59 mmol) was dissolved in 30 mL of anhydrous ethanol, and sodium borohydride (460 mg, 12.15 mmol) was added, the reaction was run at room temperature and monitored by TLC until 3 hours later when the reaction was complete, then 50 mL of water was added and 10% HCl was used to adjust pH to 2. The resulting material was extracted three times with ethyl acetate (50 mL×3), the organic layers were combined and dried over anhydrous Na2SO$_4$, the solvent was evaporated to dryness under reduced pressure, and purified with silica gel column chromatography (ethyl acetate:petroleum ether 1:1) to give 2.1 g of the compound MT-023C, yield: 96%. ESI-MS: [M−H]$^+$ m/z 288.04. $^1$H-NMR: (300 MHz, DMSO-d6) δ: 9.81 (d, J=8.1 Hz, 1H), 7.20 (m, 2H), 7.16 (m, 1H), 5.36 (q, J=8.0 Hz, 1H), 5.20 (t, J=4.5 Hz, 1H), 4.69 (t, J=5.8 Hz, 1H), 4.52 (m, 1H), 3.38 (td, J=5.8, 2.3 Hz, 2H), 2.96 (m, 1H), 2.80 (m, 1H), 2.43 (m, 1H), 1.98 (m, 1H).

Example 54. Synthesis of Compound MT-023D

Compound MT-023C (3.3 g, 11.41 mmol) was dissolved in 80 mL of 50% ethanol, stirred at room temperature, and periodic acid (2.6 g, 11.41 mmol) was added portionwise. The reaction was run for 5 minutes, then a white solid was precipitated, and the resulting mixture was filtered, and the filter residue was washed with a small amount of ice water, and dried to give 2.9 g of the compound MT-023D, yield: 99%. ESI-MS: [M−H]$^+$ m/z 256.01. $^1$H-NMR (300 MHz, DMSO-d6) δ: 10.00 (s, 1H), 9.90 (d, J=7.4 Hz, 1H), 7.83 (d, J=7.8 Hz, 1H), 7.72 (s, 1H), 7.52 (d, J=7.7 Hz, 1H), 5.44 (q, J=7.8 Hz, 1H), 3.09 (m, 1H), 2.94 (m, 1H), 2.50 (m, 1H), 2.05 (m, 1H).

Example 55. Synthesis of Compound MT-023E

Compound MT-023D (2.0 g, 7.78 mmol) was dissolved in 25 mL of DMF, NaOH (373 mg, 9.33 mmol) and propargyl bromide (0.67 mL, 8.55 mmol) were added, and the reaction was run at room temperature and monitored by TLC until 8 hours later, the reaction was complete. To the resulting material, 10 mL of water and 200 mL of ethyl acetate were added for extraction, the organic layers were combined and dried over anhydrous Na2SO$_4$. The solvent was evaporated to dryness under reduced pressure, and purified with silica gel column chromatography (ethyl acetate:petroleum ether 1:6) to give 1.95 g of the compound MT-023E, yield: 85%. $^1$H-NMR: (300 MHz, DMSO-d6) δ: Major rotamer: 9.99 (s, 1H), 7.87 (d, J=7.8 Hz, 1H), 7.79 (s, 1H), 7.56 (d, J=7.9 Hz, 1H), 5.69 (t, J=7.8 Hz, 1H), 3.85 (ddd, J=109.8, 17.5, 2.4 Hz, 2H), 3.16 (t, J=3 Hz, 1H), 3.14 (m, 1H), 3.03 (m, 1H), 2.52 (m, 1H), 2.35 (m, 1H). minor rotamer: 9.97 (s, 1H), 7.84 (d, J=7.9 Hz, 1H), 7.74 (s, 1H), 7.53 (d, J=8.2 Hz, 1H), 5.72 (t, J=7.8 Hz, 1H), 4.23 (ddd, J=78, 18, 3 Hz, 2H), 3.42 (t, J=3 Hz, 1H), 3.13 (m, 1H), 3.00 (m, 1H), 2.53 (m, 1H), 2.36 (m, 1H).

Example 56. Synthesis of Compound MT-023F

Compound MT-023E (1.0 g, 3.39 mmol) was dissolved in 20 mL of 50% ethanol solution of 0.2 N NaOH, and the reaction was run at room temperature and monitored by TLC until 3 hours later, the reaction was complete. To the resulting material, 50 mL of water and 50 mL ethyl were added for extraction, and the organic layers were combined and dried over anhydrous Na2SO$_4$. The solvent was evaporated to dryness under reduced pressure, and purified with a silica gel column chromatography (ethyl acetate:petroleum ether 1:4) to give 0.64 g of the compound MT-023F, yield: 95%. ESI-MS: [M+H]$^+$ m/z 200.03. $^1$H-NMR: (300 MHz, DMSO-d6) δ: 9.98 (s, 1H), 7.87 (s, 1H), 7.75 (d, J=7.7 Hz, 1H), 7.44 (d, J=7.7 Hz, 1H), 4.32 (t, J=6.5 Hz, 1H), 3.42 (d, J=2.4 Hz, 3H), 3.11 (t, J=2.3 Hz, 1H), 3.00 (m, 1H), 2.82 (m, 1H), 2.59 (s, 1H), 2.35 (m, 1H), 1.83 (m, 1H).

Example 57. Synthesis of Compound MT-023G

Compound MT-023D (The 0.3 g, 1.17 mmol) was added and dissolved in 20 mL of anhydrous ethanol, t-butyl hydroxylamine (208 mg, 2.33 mmol) was added, and the reaction was run at room temperature and monitored by TLC until 18 hours later, the reaction was complete. The solvent was evaporated to dryness under reduced pressure, and purified with silica gel column chromatography (ethyl acetate:petroleum ether 1:2) to give 0.37 g of the compound MT-023G, yield: 97%. ESI-MS: [M–H]$^+$ m/z 327.04. $^1$H-NMR: (300 MHz, DMSO-d6) δ: 9.84 (d, J=8.4 Hz, 1H), 8.37 (s, 1H), 8.18 (d, J=8.1 Hz, 1H), 7.87 (s, 1H), 7.32 (d, J=8.0 Hz, 1H), 5.40 (q, J=7.9 Hz, 1H), 3.01 (m, 1H), 2.86 (m, 1H), 2.57 (m, 1H), 1.98 (m, 1H), 1.49 (s, 9H).

Example 58. Synthesis of Compound MT-023

Compound MT-023F (1.0 g, 5.02 mmol) was dissolved in 50 mL of anhydrous ethanol, t-butyl hydroxylamine (895 mg, 10.4 mmol) was added, and the reaction was run at room temperature and monitored by TLC until 20 hours later, the reaction was competed. The solvent was evaporated to dryness under reduced pressure, and purified with silica gel column chromatography (ethyl acetate:petroleum ether 1:2) to give 1.22 g of the compound MT-023, yield: 90%. ESI-MS: [M+H]$^+$ m/z 271.04. $^1$H-NMR: (300 MHz, DMSO-d6) δ: 8.42 (s, 1H), 8.13 (d, J=7.9 Hz, 1H), 7.81 (s, 1H), 7.26 (d, J=7.9 Hz, 1H), 4.25 (t, J=6.2 Hz, 1H), 3.40 (d, J=1.5 Hz, 2H), 3.10 (t, J=2.4 Hz, 1H), 2.93 (m, 1H), 2.75 (m, 1H), 2.30 (m, 2H), 1.80 (m, 1H), 1.50 (s, 9H).

Example 59. Synthesis of Compound MT-024

Compound MT-023 (0.5 g, 1.85 mmol) was dissolved in 20 mL of acetone, sodium bicarbonate (186 mg, 2.22 mmol) and odomethane (115 μL, 1.85 mmol) were added, and the reaction was run at room temperature and monitored by TLC until 2 hours later, the reaction was complete. The solvent was evaporated to dryness under reduced pressure, and purified with silica gel column chromatography (ethyl acetate:petroleum ether 1:3) to give 0.32 g of the compound MT-023, yield: 61%. ESI-MS: [M+H]$^+$ m/z 284.95.

Example 60. Synthesis of Compound MT-025

Compound MT-023G (0.2 g, 0.6 mmol) was dissolved in 15 mL of 50% ethanol solution of 0.2 N NaOH, and the reaction was run at room temperature and monitored by TLC until 3 hours later, the reaction was complete, then 30 mL of water and 50 mL of ethyl acetate were added for extraction, and the organic layers were combined and dried over anhydrous Na2SO$_4$. The solvent was evaporated to dryness under reduced pressure, and purified with silica gel column chromatography (ethyl acetate) to give 0.11 g of the compound MT-025, yield: 78%. ESI-MS: [M+H]$^+$ m/z 233.08.

Example 61. Synthesis of Compound MT-026A

Toluene (10 g, 108.53 mmol), anhydrous AlCl$_3$ (20 g, 150 mmol), and acetyl chloride (9.0 g, 114.66 mmol) were placed in a mortar, and the reaction was run at stirring for 40 minutes at room temperature and monitored by TLC. Then the resulting material were added to crushed ice, extracted three times with ethyl acetate (200 mL×3), and the organic layers were combined and dried over anhydrous Na2SO$_4$. The solvent was evaporated to dryness under reduced pressure, and purified with a silica gel column chromatography (petroleum ether) to give 13.1 g of the compound MT-026A, yield: 90%. $^1$H-NMR: (300 MHz, DMSO-d6) δ: 7.87 (d, J=8.2 Hz, 2H), 7.32 (d, J=7.9 Hz, 2H), 2.55 (s, 3H), 2.38 (s, 3H). Alternatively, the crude product can be obtained without purification for further reaction.

Example 62. Synthesis of Compound MT-026B

Compound MT-026A (5.0 g, 37.26 mmol) was dissolved in 200 mL of carbon tetrachloride, NBS (2.54 g, 44.72 mmol) and benzoyl peroxide (catalytic amount) were added, and the reaction was run at reflux for 3 hours under illumination and monitored by TLC. The resulting mixture was filtrated to remove the solid, distilled under reduced pressure to remove carbon tetrachloride, and purified with a silica gel column chromatography (petroleum ether) to give 7.2 g of the compound MT-026B, yield: 91%. Alternatively, the crude product can be obtained without purification for further reaction.

Example 63. Synthesis of Compound MT-026C

Compound MT-026B (7.0 g, 32.85 mmol) was dissolved in 200 mL of glacial acetic acid, anhydrous sodium acetate (5.0 g, 60.95 mmol) was added, and the reaction was run at reflux overnight. Upon completion of the reaction, the resulting material was cooled to room temperature, and 400 mL of water and 400 mL of ethyl acetate were added for extraction, the organic layer was separated, the aqueous layer was extracted once with 400 mL of ethyl acetate, and the organic layers were combined and dried over anhydrous Na2SO$_4$. The solvent was evaporated to dryness under reduced pressure, and purified by silica gel column chromatography (ethyl acetate:petroleum ether 1:6) to give 6.3 g of the compound MT-026C, yield: 100%. ESI-MS: [M+H]$^+$ m/z 193.19. $^1$H-NMR: (300 MHz, DMSO-d6) δ: 7.96 (d, J=8.3 Hz, 2H), 7.50 (d, J=8.2 Hz, 2H), 5.16 (s, 2H), 2.58 (s, 3H), 2.10 (s, 3H). Alternatively, the crude product can be obtained without purification for further reaction.

Example 64. Synthesis of Compound MT-026D

Compound MT-026C (5.0 g, 26.01 mmol) was dissolved in 100 mL of methanol, a 25 mL aqueous solution of 8 g sodium hydroxide was added, and the reaction was run at room temperature for 30 minutes. After the reaction was complete, the resulting material was extracted with 50 mL of water and 150 mL of ethyl acetate, the organic layer was separated, the aqueous layer was extracted 3 times with ethyl acetate (50 mL×3), and the organic layers were combined and dried over anhydrous Na2SO4. The solvent was evaporated to dryness under reduced pressure, and purified with silica gel column chromatography (ethyl acetate:petroleum ether 2:3) to give the compound MT-026D 3.8 g, yield: 97%. $^1$H-NMR: (300 MHz, DMSO-d6) δ: 7.93 (d, J=8.2 Hz, 1H), 7.46 (d, J=8.2 Hz, 1H), 5.39 (s, 1H), 4.59 (s, 2H), 2.57 (s, 3H).

Example 65. Synthesis of Compound MT-026E

Compound MT-026D (3.0 g, 19.98 mmol) was dissolved in 100 mL of methanol, propargylamine (1.65 g, 29.96 mmol) was added, concentrated hydrochloric acid was used to adjust pH to neutral, sodium cyanoborohydride (2.51 g, 39.95 mmol) was added, the reaction was refluxed overnight and monitored by TLC. The resulting mixture was filtered to remove solid, the solvent was evaporated to dryness under reduced pressure, 100 mL of ethyl acetate and 100 mL of water were added for extraction, the organic layer was separated and dried over anhydrous $Na_2SO_4$. The solvent was evaporated to dryness under reduced pressure, and purified with silica gel column chromatography (ethyl acetate:petroleum ether 1:1) to give the compound MT-026E 2.9 g, yield: 77%. ESI-MS: [M+H]$^+$ m/z 189.72. $^1$H-NMR: (300 MHz, DMSO-d6) δ: 7.25 (s, 4H), 5.11 (t, J=5.7 Hz, 1H), 4.46 (d, J=5.7 Hz, 2H), 3.87 (q, J=6.4 Hz, 1H), 3.08 (dd, J=84.0, 15.0 Hz, 2H), 3.03 (t, J=2.4 Hz, 1H), 2.40 (s, 1H), 1.22 (d, J=6.6 Hz, 3H).

Example 66. Synthesis of Compound MT-026F

Compound MT-026E (3.0 g, 15.85 mmol) was dissolved in 50 mL of ethyl acetate, and activated manganese dioxide (5.51 g, 63.41 mmol) was added, and the reaction was refluxed for 5 hours and monitored by TLC, and then cooled to room temperature. The resulting mixture was filtered to remove solid, the solvent was evaporated to dryness under reduced pressure, and purified with silica gel column chromatography (ethyl acetate:petroleum ether 1:3) to give 2.8 g of the compound MT-026F, yield: 94%. ESI-MS: [M+H]$^+$ m/z 188.19. $^1$H-NMR: (300 MHz, DMSO-d6) δ: 10.01 (s, 1H), 7.89 (d, J=8.2 Hz, 2H), 7.58 (d, J=8.2 Hz, 2H), 4.03 (q, J=6.6 Hz, 1H), 3.15 (ddd, J=84.0, 17.0, 2.6 Hz, 2H), 3.08 (t, J=2.4 Hz, 1H), 2.64 (s, 1H), 1.28 (d, J=6.6 Hz, 3H).

Example 67. Synthesis of Compound MT-026

Compound MT-026F (1.0 g, 5.34 mmol) was dissolved in methanol (30 mL), t-butyl hydroxylamine (952 mg, 10.68 mmol) was added, and reaction was run at room temperature and monitored by TLC until 20 hours later, the reaction was complete. The resulting material was distilled to dryness under reduced pressure to evaporate ethanol, and purified with silica gel column chromatography (acetone: petroleum ether 1:4) to give the compound MT-026 (1.25 g, yield 90%). ESI-MS: [M+H]$^+$ m/z 259.23. $^1$H-NMR: (300 MHz, DMSO-d6) δ: 8.31 (d, J=8.3 Hz, 2H), 7.81 (s, 1H), 7.36 (d, J=8.3 Hz, 2H), 3.91 (q, J=6.5 Hz, 1H), 3.10 (ddd, J=84.0, 16.9, 2.4 Hz, 2H), 3.04 (t, J=2.4 Hz, 1H), 2.49 (s, 1H), 1.50 (s, 9H), 1.24 (d, J=6.6 Hz, 3H).

Example 68. Synthesis of Compound MT-027

Compound MT-026 (0.5 g, 1.94 mmol) was dissolved in 20 mL of acetone, sodium bicarbonate (162 mg, 1.94 mmol) and iodomethane (125 µL, 1.94 mmol) were added, and the reaction was run at room temperature and monitored by TLC until 2 hours later, the reaction was complete. The solvent was evaporated to dryness under reduced pressure, and the resulting material was purified with silica gel column chromatography (acetone: petroleum ether 1:5) to give the compound MT-027 (0.37 g, yield 70%). ESI-MS: [M+H]$^+$ m/z 273.24. $^1$H-NMR: (300 MHz, DMSO-d6) δ: 8.30 (d, J=8.3 Hz, 2H), 7.82 (s, 1H), 7.34 (d, J=8.3 Hz, 2H), 3.53 (q, J=6.6 Hz, 1H), 3.29 (ddd, J=84.0, 16.9, 2.4 Hz, 2H), 3.16 (t, J=2.4 Hz, 1H), 2.16 (s, 3H), 1.50 (s, 9H), 1.27 (d, J=6.6 Hz, 3H).

Example 69. Synthesis of Compound MT-028A (R)-(+)-1-(3-methoxyphenyl) ethylamine (4.00 g, 26.45 mmol) was placed in a 100 mL thick-walled pressure bottle, 40 mL of HBr (48% w/w in $H_2O$) was added, and the reaction was stirred for 6 hours at 100° C., and concentrated under reduced pressure to give a crude compound MT-281 as a brown oil, ESI-MS: [M+H]$^+$ 138.21. The crude product was used without purification for further reaction.

Example 70. Synthesis of Compound MT-028B

In a 50 mL round-bottom flask, the crude compound MT-281 (1.60 g) was dissolved in 25 mL of acetonitrile, anhydrous potassium carbonate (2.50 g, 18.09 mmol) was added, stirred thoroughly, then propargyl bromide (850 mg, 7.15 mmol) was added slowly dropwise, and stirred further at room temperature for 36 hours, filtered, and 2.5 g of 100-200 mesh silica gel was added, dried with spin, and purified with silica gel column chromatography (ethyl acetate:petroleum ether=2:3) to give the compound MT-282 as a white solid (440 mg, yield 34.45%). ESI-MS: [M+H]$^+$ 176.20: $^1$H-NMR (DMSO-d6): 9.26 (s, 1H), 7.08 (t, J=8.0 Hz, 1H), 6.72 (d, J=1.8 Hz, 1H), 6.71 (d, J=6.0 Hz, 1H), 6.60 (m, 1H), 3.78 (q, J=6.5 Hz, 1H), 3.21 (dd, J=16.9, 2.6 Hz, 1H), 3.03 (t, J=2.4 Hz, 1H), 2.96 (dd, J=16.9, 2.5 Hz, 1H), 2.43 (s, 1H), 1.19 (d, J=6.6 Hz, 3H).

Example 71. Synthesis of Compound MT-028

In a 50 mL round-bottom flask, compound MT-282 (440 mg, 2.51 mmol) was added and dissolved with 30 mL of anhydrous methylene chloride, 57%-63% NaH (120 mg) was added, then N-ethyl methyl carbamyl chloride (305 mg, 2.51 mmol) was added slowly dropwise, and the reaction was stirred at room temperature for 24 hours, and when the reaction was complete, the resulting material was added with 10 mL of ice water, stirred for 5 min, and extracted with dichloromethane three times (20 mL×3), the organic layers were combined and dried over anhydrous sodium sulfate, concentrated under reduced pressure, and purified with silica gel column chromatography (ethyl acetate:petroleum ether=1:2, containing 1% triethylamine) to give the compound MT-028 as a pale yellow oil (340 mg, yield 52%). ESI-MS: [M+H]$^+$ 261.21; $^1$H-NMR (DMSO-d6): 7.31 (t, J=7.8 Hz, 1H), 7.15 (dt, J=7.7, 1.3 Hz, 1H), 7.04 (t, J=2.0 Hz, 1H), 6.96 (ddd, J=8.1, 2.3, 1.1 Hz, 1H), 3.89 (q, J=6.5 Hz, 1H), 3.42 (q, J=7.2 Hz, 1H), 3.31 (q, J=7.2 Hz, 1H), 3.23 (dd, J=16.9, 2.5 Hz, 1H), 3.04 (t, J=2.4 Hz, 1H), 2.97 (dd, J=17.0, 2.3 Hz, 1H), 2.96 (d, J=36.6 Hz, 3H), 2.52 (s, 1H), 1.22 (d, J=6.6 Hz, 3H), 1.14 (dt, J=24.0, 7.1 Hz, 3H).

Example 72. Synthesis of Compound MT-029

In a 50 mL round-bottom flask, compound MT-028 (620 mg, 2.38 mmol) was added and dissolved with 30 mL of acetone, sodium hydrogen carbonate (300 mg, 3.57 mmol) was added, then iodomethane (388 mg, 2.74 mmol) was added slowly dropwise, and the reaction was stirred at room temperature for 6 hours. "The resulting mixture was filtered, concentrated under reduced pressure and purified with silica gel column chromatography (ethyl acetate:petroleum ether=1:3) to give the compound MT-029 as a pale yellow oil (198 mg, yield 30.3%). ESI-MS: [M+H]$^+$ 275.22; $^1$H-NMR (DMSO-d6): 7.32 (t, J=7.8 Hz, 1H), 7.14 (dt, J=7.7, 1.4 Hz, 1H), 7.03 (s, 1H), 6.98 (m, 1H), 3.51 (q, J=6.6 Hz, 1H), 3.42 (dd, J=16.9, 2.5 Hz, 1H), 3.41 (q, J=7.2 Hz, 1H), 3.31 (q, J=7.2 Hz, 1H), 3.18 (dd, J=16.9, 2.5 Hz, 1H), 2.95 (d, J=36.6 Hz, 3H), 2.16 (s, 3H), 1.26 (d, J=6.6 Hz, 3H), 1.14 (dt, J=24.0, 7.1 Hz, 3H).

Example 73. Synthesis of Compound MT-030A

In a 100 mL thick-walled pressure bottle, (S)-(−)-1-(3-methoxyphenyl) ethylamine (3.04 g, 20.10 mmol) was placed, 30 mL of HBr (48% w/w in H$_2$O) was added, and the reaction was stirred at 100° C. for 6 hours, and concentrated under reduced pressure to give crude compound MT-301 as a brown oil, ESI-MS: [M+H]$^+$ 138.02. Used without purification for further reaction.

Example 74. Synthesis of Compound MT-030B

To a 100 mL round-bottom flask, crude compound MT-301 (3.00 g) was added and dissolved in 45 mL of acetonitrile, anhydrous potassium carbonate (8.00 g, 57.89 mmol) was added, stirred thoroughly, propargyl bromide (2.60 g, 21.89 mmol) was added slowly dropwise, and continued to stir for 36 hours, and the resulting mixture was filtered, and 4.50 g of 100-200 mesh silica gel was added, spined to dry, and purified with silica gel column chromatography (ethyl acetate:petroleum ether=2:3) to give the compound MT-302 as a white solid (1.32 g, yield: 37.47%). ESI-MS: [M+H]$^+$ 176.16; $^1$H-NMR (DMSO-d6): 9.26 (s, 1H), 7.08 (t, J=8.0 Hz, 1H), 6.73 (d, J=1.8 Hz, 1H), 6.71 (d, J=6.0 Hz, 1H), 6.60 (m, 1H), 3.79 (q, J=6.5 Hz, 1H), 3.22 (dd, J=16.9, 2.6 Hz, 1H), 3.02 (t, J=2.4 Hz, 1H), 2.96 (dd, J=16.9, 2.5 Hz, 1H), 2.36 (s, 1H), 1.19 (d, J=6.5 Hz, 3H).

Example 75. Synthesis of Compound MT-030

In a 100 mL round-bottom flask, compound MT-302 (1.32 g, 7.53 mmol) was added and dissolved with 50 mL of anhydrous methylene chloride, 57%~63% NaH (412 mg) was added, then N-carbamoyl chloride (1.00 g, 8.23 mmol) was added slowly dropwise, stirred at room temperature for 24 hours. After the reaction was complete, 15 mL of ice water was added, stirred for 5 min, and extracted with dichloromethane for three times (20 mL×3), the combined organic layers were dried with anhydrous sodium sulfate, concentrated under reduced pressure and purified with silica gel column chromatography (ethyl acetate:petroleum ether=1:2, containing 1% triethylamine) to give the compound MT-030 as a pale yellow oil (930 mg, yield 47.4%). ESI-MS: [M+H]+ 261.17; 1H-NMR (DMSO-d6): 7.31 (t, J=7.8 Hz, 1H), 7.15 (dt, J=7.7, 1.4 Hz, 1H), 7.05 (t, J=2.0 Hz, 1H), 6.96 (ddd, J=8.2, 2.4, 1.1 Hz, 1H), 3.89 (q, J=6.5 Hz, 1H), 3.42 (q, J=7.5 Hz, 1H), 3.31 (q, J=7.5 Hz, 1H), 3.23 (dd, J=17.0, 2.3 Hz, 1H), 3.04 (t, J=2.4 Hz, 1H), 2.97 (dd, J=17.0, 2.3 Hz, 1H), 2.96 (d, J=36.6 Hz, 3H), 2.49 (s, 1H), 1.22 (d, J=6.6 Hz, 3H), 1.14 (dt, J=24.0, 7.1 Hz, 3H).

Example 76. Synthesis of Compound MT-031

In a 50 mL round bottom flask, compound MT-030 (570 mg, 2.19 mmol) was weighted and dissolved with 30 mL of acetone, sodium hydrogen carbonate (280 mg, 3.28 mmol) was added, iodomethane (280 mg, 2.52 mmol) was added slowly dropwise, and the reaction was stirred at room temperature for 6 hours. After the reaction was complete, the resulting material was filtered, concentrated under reduced pressure and purified with silica gel column chromatography (ethyl acetate:petroleum ether=1:3) to give the compound MT-031 as a pale yellow oil (220 mg, yield 36.6%). ESI-MS: [M+H]$^+$ 275.15; $^1$H-NMR (DMSO-d6): 7.32 (t, J=7.8 Hz, 1H), 7.14 (dt, J=7.7, 1.3 Hz, 1H), 7.03 (s, 1H), 6.98 (m, 1H), 3.51 (q, J=6.6 Hz, 1H), 3.42 (q, J=7.5 Hz, 1H), 3.41 (dd, J=17.0, 2.3 Hz, 1H), 3.31 (q, J=7.5 Hz, 1H), 3.18 (dd, J=17.0, 2.3 Hz, 1H), 3.15 (t, J=2.4 Hz, 1H), 2.96 (d, J=36.6 Hz, 3H), 2.16 (s, 3H), 1.26 (d, J=6.6 Hz, 3H), 1.14 (dt, J=23.4, 7.1 Hz, 3H).

Example 77. Synthesis of Compound HMW-3

Compound MT-019A (1.05 g, 6 mmol) was dissolved in 25 mL of dry CH$_2$Cl$_2$, a powder of NaH (0.24 g, 6 mmol) was added, the reaction was run for 2 hours, and after the solution became cloudy, N-ethyl-N-methyl-carbamoyl chloride (0.72 g, 6 mmol) was added, and the reaction was run for 3 hours and monitored by TCL. After the reaction was complete, the resulting material was extracted 3 times with CH$_2$Cl$_2$ (25 mL×3), and the organic layers were combined and dried over anhydrous Na$_2$SO$_4$, the solvent was evaporated to dryness under the pressure reduced and purified with silica gel column chromatography (ethyl acetate:petroleum ether=1:1) to give the compound HMW-3 as a colorless oil (1.6 g, 76%). ESI-MS: [M+1]+ m/z 261.1. $^1$H-NMR (DMSO-d6, 300 MHz) δ: 1.13 (m, 3H), 1.23 (d, J=6.6 Hz, 3H), 2.89 (s, 1H), 3.02 (m, 3H), 3.23 (dd, J=2.4 Hz, 16.8 Hz, 2H), 3.40 (m, 2H), 3.89 (q, J=6.6 Hz, 1H), 6.96 (dd, J=1.5 Hz, 7.8 Hz, 1H), 7.05 (s, 1H), 7.15 (d, J=7.8 Hz, 1H), 7.31 (t, J=7.8 Hz, 1H).

Example 78. Synthesis of Compound HMW-2

Compound HMW-3 (0.78 g, 3 mmol) was dissolved in 25 mL of methanol, NaHCO$_3$ (0.38 g, 4.5 mmol) and CH$_3$I (0.5 g, 4.5 mmol) were added respectively, and the reaction was run at room temperature for 3 hours and monitored by TCL. After the reaction was complete, the solvent was evaporated, aqueous NaHCO$_3$ was added to adjust pH to neutral, and the resulting material was extracted three times with ethyl acetate (25 mL×3), and the organic layers were combined and dried over anhydrous Na$_2$SO$_4$, the solvent was evaporated under reduced pressure and separated with silica gel column chromatography (ethyl ethyl ester:petroleum ether=1:2) to give the compound HMW-2 as a pale yellow oil (0.61 g, 74%). $^1$H-NMR (CDCl$_3$, 300 MHz) δ: 1.13 (m, 3H), 1.35 (d, J=6.6 Hz, 3H), 2.23 (t, 1H), 2.29 (s, 3H), 3.02 (d, 3H), 3.25 (m, 2H), 3.46 (m, 2H), 3.56 (q, J=6.6 Hz, 1H), 7.01 (m, J=6.6 Hz, 1H), 7.14 (m, 2H), 7.29 (t, 1H, J=6.6 Hz).

Example 79. Synthesis of Compound HMW-1

The compound HMW-3 (0.52 g, 2 mmol) was added and dissolved in 20 mL of methanol, NaHCO$_3$ (0.17 g, 2 mmol) and propargyl bromide (0.24 g, 2 mmol) were added respectively, the reaction was refluxed for 3 hours and monitored by TLC. After the reaction was complete, the solvent was evaporated, 20 mL of water was added, and the resulting material was extracted three times with ethyl acetate (25 mL×3), the organic layers were combined and dried over anhydrous Na$_2$SO$_4$, the solvent was evaporated under reduced pressure, and separated by silica gel column (ethyl acetate:petroleum ether=1:3) to give the compound HMW-1 as a white solid (0.43 g, 72%). ESI-MS: [M+1]$^+$ m/z 299.5. $^1$H-NMR (CDCl$_3$, 300 MHz) δ: 1.25 (m, 3H), 1.40 (d, J=6.6 Hz, 3H), 2.24 (s, 2H), 3.04 (d, J=21.9 Hz, 3H), 3.44 (m, 2H), 3.52 (d, J=2.1 Hz, 4H), 3.68 (q, J=6.6 Hz, 1H), 7.05 (d, J=7.5 Hz, 1H), 7.14 (s, 1H), 7.21 (d, J=7.5 Hz, 1H), 7.32 (t, J=7.5 Hz, 1H).

Example 80. Protective Effects of Compounds on Cerebellar Granule Cells from MPP$^+$-Induced Damages The original generation of cerebellar granule cells were taken from neonatal SD rats (7-8 day-old, 15-20 g), cultured in vitro for 7 days, and preliminarily protected for 2 hours by adding the compounds in different concentrations, respectively, wherein equal amount of culture medium was added for model control group. Consequently, MPP$^+$ in a final concentration of 150 μM was added for induction of 24 hours, wherein equal amount of culture medium was added for control group. MTT was used to detect cell activity. Rasagiline was used for control. The test results are shown in FIG. 17.

Example 81. Scavenging Effects of Compounds on Free Radicals of OH$^\bullet$, O$_2^{\bullet-}$ and DPPH Hydroxyl Radical (OH$^\bullet$):

Orthophenanthroline-metal ion-H$_2$O$_2$ was used to generate hydroxyl radical via Fenton reaction (H$_2$O$_2$+Fe$^{2+}$→OH+ H$_2$O+Fe$^{3+}$) to generate hydroxyl free radicals, causing orthophenanthroline-Fe$^{2+}$ to be oxidated to orthophenanthroline-Fe$^{3+}$, and causing its aqueous solution to show maximum disappearance at 440 nm wavelength, so as to measure the scavenging rate. A detailed process is shown as follows: In a 48-well plate was added with 300 μL of double distilled water (blank control), or a solution of AL-1 of different concentrations (dissolved in DMSO to make a 10 mM stock solution, which is then diluted with double distilled water to give solutions of 0.01 μM, 0.1 μM, 1 μM, 10 μM). A 50 μL solution of 1.0 mM orthophenanthroline (1.0 mM dissolved in 50 mM of NaCl solution) was added, and then 125 μL of 1.0 mM H$_2$O$_2$ and 125 μL, of 2.0 mM Fe$^{2+}$ were added respectively and then mixed thoroughly. A microplate reader of BioTek Synergy HT was used to measure absorbance reduction percentage at 440 nm within 100 seconds. The scavenging rate of hydroxyl radical can be calculated as: Scavenging Rate (%)=[1−(A$_0$−A$_{100}$)/A$_0$]× 100%, wherein A$_0$ and A$_{100}$ are absorbance values of 0 and 100 seconds, respectively.

Free Radical of Superoxide Anion (O$_2^{\bullet-}$):

Method of 1,2,3-Trihydroxybenzene autoxidation was used, and the detailed process is shown as follows: In a 48-well plate was added with 250 μL of 50 mM Tris-HCl buffer (pH 8.2), 300 μL of double distilled water (blank control), or a solution of AL-1 of different concentrations (dissolved in DMSO to make a 10 mM stock solution, which was then diluted with double distilled water to give solutions of 0.01 μM, 0.1 μM, 1 μM, 10 μM). A 50 μL solution of 2.0 mM 1,2,3-Trihydroxybenzene was added, and mixed thoroughly with a vortex mixer. Results were compared with blank at 320 nm wavelength, and recorded every 30 seconds. A microplate reader of BioTek Synergy HT was used to measure absorbance values continually for 30 minutes. Absorbance values of the samples were also measured under the same conditions, while oxidation rate refers to the increase of the absorbance value per minute. Linear regression method was used, wherein, graphs were prepared with a coordinate having a horizontal axis for time (seconds) and a vertical axis for absorbance, to obtain the linear relationship between absorbance values and time, and the autoxidation rate of 1,2,3-Trihydroxybenzene was calculated to obtain results indicated by dA/dt, increment of absorbance per second, i.e., the value a in the equation of linear regression of y=ax+b. Scavenging rate (%)=(dA/dt−dAs/dt)/ (dA/dt), wherein dA/dt refers to the autooxidatio rate of 1,2,3-Trihydroxybenzene under the condition in absence of samples, and dAs/dt refers to the autooxidatio rate of 1,2, 3-Trihydroxybenzene under the condition in presence of samples.

Free Radical of 1,1-Diphenyl-2-Phenylhydrazine (DPPH):

The spectroscopic measurement of free radicals of 1,1-diphenyl-2-phenylhydrazine (DPPH) is based on that DPPH has a strong absorption at 517 nm, and the methanol solution of which shows a dark purple color. When a free radical scavenger exists, its absorbance disappears gradually due to single electron pairing, and the extent of color fading has a quantitative relationship with the number of electrons. Thus, the quantitative analysis can be performed based on the change in absorbance before and after the reaction, and, by measuring the change of absorbance of each sample towards DPPH, the scavenging rate can then be taken as an indication of the ability of scavenging free radicals. The tests were performed as follows: In a 96-well plate were added with 100 μL of samples in various concentrations (sample group) or 100 μL of methanol (blank control group). Then a 100 μL solution of 100 μM DPPH in methanol was added rapidly (with a final concentration of 50 μM), with each of the samples placed in 3-5 wells of replicas, and the samples were vibrated and placed in the dark at room temperature for one hour, and then the absorbance values were measured at 517 nm with a microplate reader. The scavenging rates were calculated by:

$$\text{Scavenging Rate (\%)}=(A_{ctrl}-A_{sample})/A_{ctrl}\times 100\%.$$

Example 82. In Vitro Inhibitory Activities of Compounds to MAO-A/B

MAO-A/B was taken from SD mouse brain, the compound was dissolved in various concentrations in a buffer, in case that the compound was used to test the inhibitory activity to MAO-A, then 0.05 μM of deprenyl (MAO-B inhibitor) was added, and in case that the compound was used to test the inhibitory activity to MAO-B, then 0.05 μM of clorgylin (MAO-A inhibitors) was added. Brain homogenate was added, incubated for 30 min at 37° C., and $^{14}$C-5-hydroxytryptamine (MAO-A) and $^{14}$C-phenylethylamine (MAO-B) were added respectively. The inhibitory activity of the compound to MAO-A or MAO-B was determined.

Example 83. In Vivo Inhibitory Effect of Compounds to MAO-A/B

Compound HMW-2 (2.5, 5, 10 mg/kg) were given via intraperitoneal injection to mices respectively, an equivalent amount of saline was injected for the control group, then the mices were terminated 1 or 2 hours thereafter, the activity of MAO-A/B in cerebellum, liver and small intestine was determined respectively.

Example 84. In Vitro Inhibitory Effect of Compound to Cholinesterase

Ellman's method was used to measure the cholinesterase activity, wherein 20 μL of various concentrations of the compound and the brain tissue were incubated at 37° C. for 3 hours, then a 180 μL of mixed solution of DTNB and ATCh or BTCh was added, and immediately the change of absorbance within 10 minutes was measured at 412 nM wavelength to give a kinetics curve. The inhibitory effect of the compound to cholinesterase is calculated based on the slope of the curve.

Example 85. In Vitro Inhibitory Effect of Compound HMW-2 to Cholinesterase

Compound HMW-2 (2.5, 5, 10 or 25 mg/kg) were given via intraperitoneal injection to mices respectively, an equivalent amount of saline was injected for the control group, then the mices were terminated 2 hours thereafter, and the activated of AChE and BuChE in cerebral cortex and liver were determined respectively.

Example 86. The Recovering Effect of Compound MT-019 to MPTP-Induced Abnormal Behavior of Mice of Parkinson's Disease (PD) Model Forty of C57BL/6J mice (male, 6 to 7 week-old) were feed for 7 days to adapt to the environment. On the day 8, animal model was started to prepare. 20 mg/kg MPTP was given via intraperitoneal injection for the model group and drug group, the injection was made every 2 hours, for four times in total, and an acute PD model was established. The equivalent amount of saline was given to the normal control group. From the day 2 of model establishment, the compound MT-019 and the positive control drug Rasagiline (1 mg/kg) were given. The doses of MT-019 were 25, 75, 225 mg/kg, respectively. The drug was given once a day, and a equal amount of saline was given to the normal control group and the MPTP model group, for seven days consecutively. On the day 7 of drug administration, behavioral test is performed. The results showed that the compound MT-019 had recovery effect to MPTP induced abnormal behavior of mice of Parkinson's disease (PD) model.

Example 87. Protective Effect of the Compound MT-019 on TH Neurons in SNpc Area of MPTP Induced Mice of Parkinson's Disease (PD) Model After the above-mentioned animal model was set up and drug was given to the mice as described in Example 86, materials was taken at 12 hours after the last drug administration in the steps shown below: (1) With 10% chloral hydrate anesthesia in mice, the mice were fixed on an operating table, the chest thereof was quickly open; (2) a needle was inserted from, a needle was inserted from the left ventricle, the right auricle was cut open, and a blood buffer was delivered to the heart from an infusion bottle with a volume of about 50 mL per mouse; (3) after the lavage fluid became colorless, the blood buffer was replaced with 4% paraformaldehyde solution in perfusion until the tail and limbs of the mice became stiff, wherein the infusion volume was about 100 mL per mouse; (4) the brain was taken by making the mice beheaded on a flat glass board, and redundant parts were carefully removed. The midbrain was placed and fixed in a centrifuge tube containing freshly prepared 4% paraformaldehydea. The samples were cut into paraffin sections through the process of dehydrating, transparent, paraffining and embedding steps. Each of the samples was cut with paraffin slicing machine into four microns slices. After fully unfold in water bath, the slices were put on glass plates and numbered.

The slices from the top position between 3.08 to 3.20 microns were selected as the group for immunohistochemistry, the procedure of which is shown as follows:

1. Dewaxing and rehydration: The tissue slices were placed at room temperature, and was put into the vat with xylene and soaked for 10 minutes, and then was transferred into another vat with xylene and soaked for another 10 minutes. After completion of the dewaxing process, the tissue slices were sequentially put in anhydrous 95%, 85%, 75% and 50% ethanol, and respectively treated for 5 minutes. After the hydration process, the tissue slices were put in pure water, treated for 5 minutes, then transferred to a PBS buffer to be treated for 5 minutes.

2. Antigen repairing: Prior to antigen epitope repairing, quenching treatment is required for endogenous peroxidase: the slices were dropped with a 3% hydrogen peroxide solution, then incubated in a wet box for 10 minutes, at this point, the endogenous peroxidase may be inhibited by hydrogen peroxide. After the treatment, washed three times with PBS for 5 minutes each time, to wash away the residual hydrogen peroxide. The slices were placed in a 0.01 M citrate buffer, microwave oven heated to boiling and maintained for 8 minutes, taken out and allowed to return to room temperature, then rinsed two times with PBS for 5 minutes each time.

3. Immune response: The residual PBS was removed with filter paper, dropped with 10% PBS diluted goat serum, enclosed in wet box at room temperature for 30 to 60 minutes. After incubation, the sealing fluid was removed (10% normal horse serum), dropped with a first antibody solution, placed in the wet box, incubated at 4° C. overnight. The next day, the first antibody was removed, rinsed 2 times with PBS for 10 minutes each time. The residual solution was wiped out, dropped with a second antibody solution, incubated for 30 minutes at the room temperature. The second antibody solution was removed, rinsed twice with PBS for 10 minutes each time.

4. Chemical dyeing: The residual PBS was removed with filter paper, dropped with freshly prepared DAB solution, incubated in a wet box, and the dyeing levels was observed with a microscope. After the dyeing, the material was soaked with PBS and rinsed three times for 5 minutes each time.

5. Dehydration and sealing: Unlike the rehydration process, the material was firstly placed in 50% ethanol for 5 minutes, then sequentially in 75%, 85%, 95% ethanol and anhydrous ethanol for 5 minutes respectively, and finally put in xylene for transparent treatment 2 times, each time for 10 minutes. After the dehydration treatment, the residual solution around the slices was wiped out, added with one drop of neutral resin, covered with a glass plate, to complete the slice sealing process.

Figure 26:
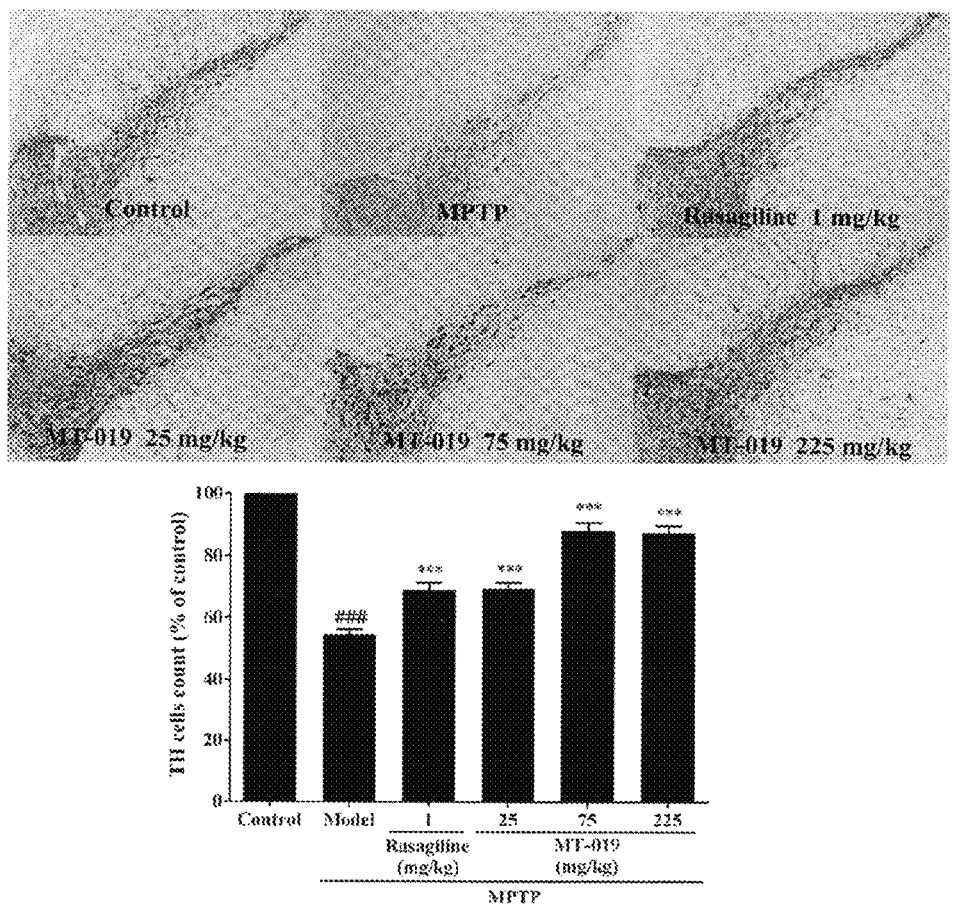
FIG. 26, in accordance to an embodiment of the present invention, illustrates the protective effect of the compound of MT-019 to SNpc area TH neurons in MPTP induced Parkinson's disease (PD) mouse models. Micrograph and data graph are shown respectively on the top and bottom portions.

Six slices from the same position in substantia nigra compact area were obtained from each of the mice, photos were taken under a 50-time microscope. Positive cells in the substantia nigra area were counted, average value was taken for each photo, and comparison was made among the groups of the cell numbers. The results showed that the compound MT-019 had protective effect on the SNpc area TH neurons of MPTP-induced Parkinson's (PD) mice model, and the protectice effect of 25 mg/kg of MT-019 to dopaminergic neurons was shown to be equivalent to that of the positive control drug Rasagiline 1 mg/kg, and also showed that stronger effect was indicated with higher doses (see FIG. 26).

Although particular embodiments have been herein described in detail, the above description has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims.

The invention claimed is:

1. A compound with neural protective effect, which has a general structure of formula (V):

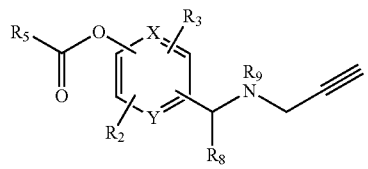

(V)

or a pharmaceutically acceptable salt thereof, wherein:
X and Y both are CH;
$R_2$ and $R_3$ are each independently hydrogen, alkyl, ester group, or substituted or unsubstituted urethane group, nitronyl group or propargyl amino group;
$R_5$ is substituted or unsubstituted amino, alkyl, aryl or heteroaryl group, wherein the amino is —$NR_6R_7$ with $R_6$ and $R_7$ being each independently hydrogen or alkyl; and
$R_8$ and $R_9$ are each independently hydrogen, methyl, ethyl or propargyl group, wherein $R_8$ is not linked with $R_2$ or $R_3$ to form a ring.

2. The compound of claim 1, wherein $R_5$ is amino, such that the compound has a general structure of formula (VII):

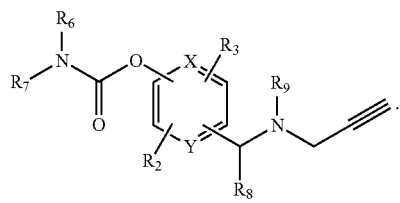

(VII)

wherein: $R_2$ and $R_3$ are each independently hydrogen or alkyl.

3. The compound of claim 2, which is selected from the group consisting of:

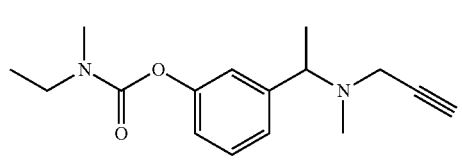

HMW-2

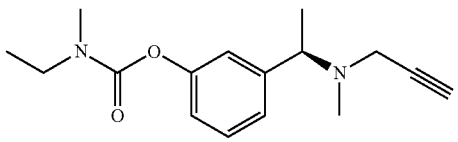

MT-029

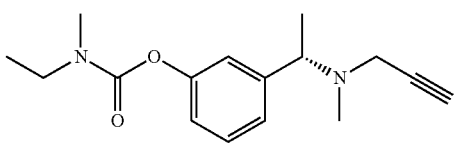

MT-031

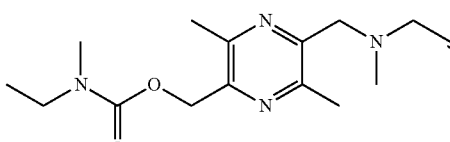

MT-009

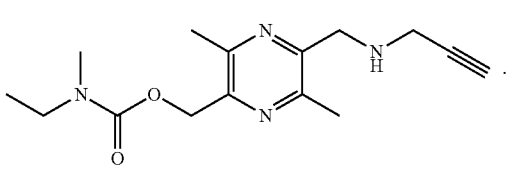

MT-010

4. The compound of claim 1, wherein $R_2$ is

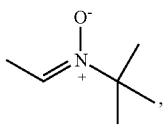

such that the compound has a general structure of formula (IX):

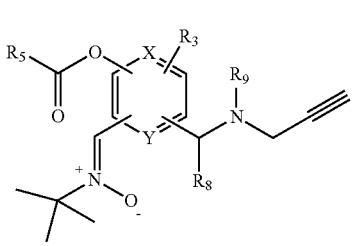

(IX)

wherein:
$R_3$ is hydrogen, alkyl, ester group, or substituted or unsubstituted urethane group, nitronyl group or propargyl amino group;
$R_5$ is substituted or unsubstituted amino, alkyl, aryl or heteroaryl group; and
$R_8$ and $R_9$ are each independently hydrogen, methyl, ethyl or propargyl group, wherein $R_8$ is not linked with $R_3$ to form a ring.

5. The compound of claim 4, wherein $R_5$ is amino, such that the compound has a general structure of formula (X):

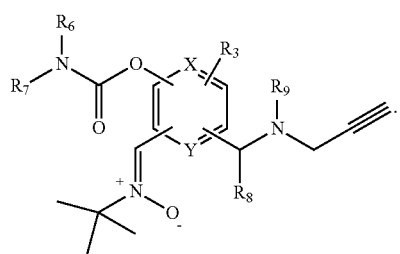
(X)
wherein: $R_6$ and $R_7$ are each independently hydrogen or alkyl.
6. The compound of claim 5, which is selected from the group consisting of following compounds:
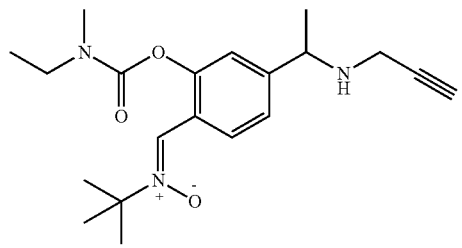
MT-019
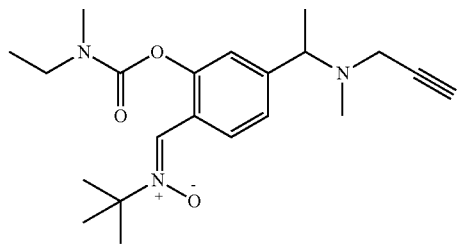
MT-020
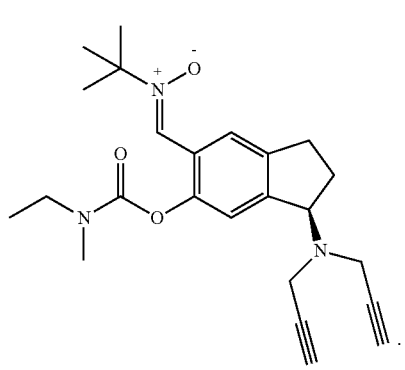
MT-022
* * * * *